(12) United States Patent
Caggiano et al.

(10) Patent No.: US 6,713,607 B2
(45) Date of Patent: Mar. 30, 2004

(54) EFFECTOR PROTEINS OF RAPAMYCIN

(75) Inventors: Thomas J. Caggiano, Morrisville, PA (US); Yanqiu Chen, New York, NY (US); Amedeo A. Failli, Princeton, NJ (US); Katherine L. Molnar-Kimber, Glenside, PA (US); Koji Nakanishi, New York, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/950,634

(22) Filed: Sep. 13, 2001

(65) Prior Publication Data

US 2003/0032775 A1 Feb. 13, 2003

Related U.S. Application Data

(63) Continuation of application No. 08/471,112, filed on Jun. 6, 1995, now Pat. No. 6,313,264, which is a continuation-in-part of application No. 08/384,524, filed on Feb. 13, 1995, now abandoned, which is a continuation-in-part of application No. 08/312,023, filed on Sep. 26, 1994, now abandoned, which is a continuation-in-part of application No. 08/207,975, filed on Mar. 8, 1994, now abandoned.

(51) Int. Cl.[7] .................................................. C07K 1/00
(52) U.S. Cl. ....................................................... 530/350
(58) Field of Search ......................................... 530/350

(56) References Cited

U.S. PATENT DOCUMENTS

| 5,109,112 A | 4/1992 | Siekierka et al. |
| 6,127,521 A | 10/2000 | Berlin et al. |
| 6,150,137 A | 11/2000 | Berlin et al. |
| 6,464,974 B1 | 10/2002 | Berlin et al. |

FOREIGN PATENT DOCUMENTS

| EP | 0379342 | 7/1990 |
| EP | 0481673 | 4/1992 |
| WO | 92/18527 | 10/1992 |
| WO | 92/19745 | 11/1992 |
| WO | 93/07269 | 4/1993 |
| WO | 93/25533 | 12/1993 |

OTHER PUBLICATIONS

Chen, et al., "A Putative Sirolimus (Rapamycin) Effector Protein," *Biochemical and Biophysical Research Communications*, vol. 203, No. 1, 1–7 (1994).
Sabatini, et al., "Identification of a Target for FKBP12–Rapamycin From Mammalian Brain," *Society for Neuroscience Abstracts*, 20(1–2) (Abstract 49.10) (1994).
Armistead et al., Annual Rpt In Med. Chem., 28:207–215 (1993).
Belshaw et al., Synlett, 6:381–464 (1994).
Brown et al., Nature, 369:756–758 (1994).
Cafferkey et al., Molecular and Cellular Biology, 13(10):6012–6023 (1993).
Chen et al., PNAS, 92:4947–4951 (1995).
Chiu et al., PNAS, 91:12574–12578 (1994).
Clardy, PNAS, 92:56–61 (1995).
Current Opinion in Therapeutic Patents, pp. 37–38, Jan. 1992.
Erdjument–Bromage et al., Protein Science, 3:2435–2446 (1994).
Heitman et al., Reports, 253 905–909 (1991).
Kivisto, Clin. Pharmacokinet, 23(3):173–190 (1992).
Kunz et al., Cell, vol. 73:585–596 (1993).
Kunz et al., Trends in Biochemical Sciences, 18:334–338 (1993).
Liu, TIPS, vol. 14:182–188 (1993).
Liu et al., Cell, vol. 66:807–815 (1991).
Milligan et al., J. Med. Chem., 36(14):1923–1937 (1993).
Murthy et al., Clin. Chem., vol. 38, No. 7:1307–1310 (1992).
Ocain et al., Biochem. and Biophys. Res. Comm., 192(3):1340–1346 (1993).
Partaledis et al., Yeast, 8:673–680 (1992).
Rosen et al., Angew, Chem. Int. Ed. Engl., 31:384–400 (1992).
Sabatani et al., Cell, 78:35–43 (1994).
Sabers et al., J. Biol. Chem., 270:815–822 (1995).
Seghal et al., Medicinal Research Reviews, vol. 14, No. 1:1–22(1994).
Seghal et al., Therapeutic Drug Monitoring, 17:660–665 (1995).

*Primary Examiner*—Ponnathapu Achutamurthy
*Assistant Examiner*—Kathleen Kerr
(74) *Attorney, Agent, or Firm*—Finnegan, Henderson, Farabow, Garrett & Dunner, L.L.P.

(57) ABSTRACT

This invention comprises novel Rapamycin-FKBP12 binding proteins of mammalian origin for identification, design and synthesis of immunomodulatory, anti-restenosis or anti-tumor agents, as well as fragments of the proteins and the DNA, cDNA, antisense RNA and DNA segments corresponding to the proteins. This invention also comprises methods for isolating the proteins and therapeutic uses related to the proteins.

3 Claims, No Drawings

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
        (A) LENGTH: 7653 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO: 1:

```
AAGATGCTTG GAACCGGACC TGCCGCCGCC ACCACCGCTG CCACCACATC TAGCAATGTG  60

AGCGTCCTGC AGCAGTTTGC CAGTGGCCTA AAGAGCCGGA ATGAGGAAAC CAGGGCCAA  120

GCCGCCAAGG AGCTCCAGCA CTATGTCACC ATGGAACTCC GAGAGATGAG TCAAGAGGA  180

TCTACTCGCT TCTATGACCA ACTGAACCAT CACATTTTTG AATTGGTTTC CAGCTCAGA  240

GCCAATGAGA GGAAAGGTGG CATCTTGGCC ATAGCTAGCC TCATAGGAGT GGAAGGTGG  300

AATGCCACCC GAATTGGCAG ATTTGCCAAC TATCTTCGGA ACCTCCTCCC CTCCAATGA  360

CCAGTTGTCA TGGAAATGGC ATCCAAGGCC ATTGGCCGTC TTGCCATGGC AGGGGACAC  420

TTTACCGCTG AGTACGTGGA ATTTGAGGTG AAGCGAGCCC TGGAATGGCT GGGTGCTGA  480

CGCAATGAGG GCCGGAGACA TGCAGCTGTC CTGGTTCTCC GTGAGCTGGC CATCAGCGT  540

CCTACCTTCT TCTTCCAGCA AGTGCAACCC TTCTTTGACA ACATTTTTGT GGCCGTGTG  600
```

```
GACCCCAAAC AGGCCATCCG TGAGGGAGCT GTAGCCGCCC TTCGTGCCTG TCTGATTCT 660
ACAACCCAGC GTGAGCCGAA GGAGATGCAG AAGCCTCAGT GGTACAGGCA CACATTTGA 720
GAAGCAGAGA AGGGATTTGA TGAGACCTTG GCCAAAGAGA AGGGCATGAA TCGGGATGA 780
CGGATCCATG GAGCCTTGTT GATCCTTAAC GAGCTGGTCC GAATCAGCAG CATGGAGGG 840
GAGCGTCTGA GAGAAGAAAT GGAAGAAATC ACACAGCAGC AGCTGGTACA CGACAAGTA 900
TGCAAAGATC TCATGGGCTT CGGAACAAAA CCTCGTCACA TTACCCCCTT CACCAGTTT 960
CAGGCTGTAC AGCCCCAGCA GTCAAATGCC TTGGTGGGGC TGCTGGGGTA CAGCTCTC 1020
CAAGGCCTCA TGGGATTTGG GACCTCCCCC AGTCCAGCTA AGTCCACCCT GGTGGAGA 1080
CGGTGTTGCA GAGACTTGAT GGAGGAGAAA TTTGATCAGG TGTGCCAGTG GGTGCTGA 1140
TGCAGGAATA GCAAGAACTC GCTGATCCAA ATGACAATCC TTAATTTGTT GCCCCGCT 1200
GCTGCATTCC GACCTTCTGC CTTCACAGAT ACCCAGTATC TCCAAGATAC CATGAACC 1260
GCCCTAAGCT GTGTCAAGAA GGAGAAGGAA CGTACAGCGG CCTTCCAAGC CCTGGGGC 1320
CTTTCTGTGG CTGTGAGGTC TGAGTTTAAG GTCTATTTGC CTCGCGTGCT GGACATCA 1380
CGAGCGGCCC TGCCCCCAAA GGACTTCGCC CATAAGAGGC AGAAGGCAAT GCAGGTGG 1440
GCCACAGTCT TCACTTGCAT CAGCATGCTG GCTCGAGCAA TGGGGCCAGG CATCCAGC 1500
GATATCAAGG AGCTGCTGGA GCCCATGCTG GCAGTGGGAC TAAGCCCTGC CCTCACTG 1560
GTGCTCTACG ACCTGAGCCG TCAGATTCCA CAGCTAAAGA AGGACATTCA AGATGGGC 1620
CTGAAAATGC TGTCCCTGGT CCTTATGCAC AAACCCCTTC GCCACCCAGG CATGCCCA 1680
GGCCTGGCCC ATCAGCTGGC CTCTCCTGGC CTCACGACCC TCCCTGAGGC CAGCGATG 1740
GGCAGCATCA CTCTTGCCCT CCGAACGCTT GGCAGCTTTG AATTTGAAGG CCACTCTC 1800
ACCCAATTTG TTCGCCACTG TGCGGATCAT TTCCTGAACA GTGAGCACAA GGAGATC 1860
ATGGAGGCTG CCCGCACCTG CTCCCGCCTG CTCACACCCT CCATCCACCT CATCAGTG 1920
CATGCTCATG TGGTTAGCCA GACCGCAGTG CAAGTGGTGG CAGATGTGCT TAGCAAAC 1980
CTCGTAGTTG GGATAACAGA TCCTGACCCT GACATTCGCT ACTGTGTCTT GGCGTCCC 2040
GACGAGCGCT TTGATGCACA CCTGGCCCAG GCGGAGAACT GCAGGCCTT GTTTGTGG 2100
CTGAATGACC AGGTGTTTGA GATCCGGGAG CTGGCCATCT GCACTGTGGG CCGACTCA 2160
AGCATGAACC CTGCCTTTGT CATGCCTTTC CTGCGCAAGA TGCTCATCCA GATTTTGA 2220
GAGTTGGAGC ACAGTGGGAT TGGAAGAATC AAAGAGCAGA GTGCCCGCAT GCTGGGGC 2280
CTGGTCTCCA ATGCCCCCCG ACTCATCCGC CCCTACATGG AGCCTATTCT GAAGGCAT 2340
ATTTTGAAAC TGAAAGATCC AGACCCTGAT CCAAACCCAG GTGTGATCAA TAATGTCC 2400
GCAACAATAG GAGAATTGGC ACAGGTTAGT GGCCTGGAAA TGAGGAAATG GGTTGATG 2460
CTTTTTATTA TCATCATGGA CATGCTCCAG GATTCCTCTT TGTTGGCCAA AAGGCAGG 2520
GCTCTGTGGA CCCTGGGACA GTTGGTGGCC AGCACTGGCT ATGTAGTAGA GCCCTACA 2580
AAGTACCCTA CTTTGCTTGA GGTGCTACTG AATTTTCTGA AGACTGAGCA GAACCAGG 2640
ACACGCAGAG AGGCCATCCG TGTGTTAGGG CTTTTAGGGG CTTTGGATCC TTACAAGC 2700
AAAGTGAACA TTGGCATGAT AGACCAGTCC CGGGATGCCT CTGCTGTCAG CCTGTCAG 2760
TCCAAGTCAA GTCAGGATTC CTCTGACTAT AGCACTAGTG AAATGCTGGT CAACATGG 2820
AACTTGCCTC TGGATGAGTT CTACCCAGCT GTGTCCATGG TGGCCCTGAT GCGGATCT 2880
CGAGACCAGT CACTCTCTCA TCATCACACC ATGGTTGTCC AGGCCATCAC CTTCATCT 2940
```

-continued

```
AAGTCCCTGG GACTCAAATG TGTGCAGTTC CTGCCCCAGG TCATGCCCAC GTTCCTTA 3000
GTCATTCGAG TCTGTGATGG GGCCATCCGG GAATTTTTGT TCCAGCAGCT GGGAATGT 3060
GTGTCCTTTG TGAAGAGCCA CATCAGACCT TATATGGATG AAATAGTCAC CCTCATGA 3120
GAATTCTGGG TCATGAACAC CTCAATTCAG AGCACGATCA TTCTTCTCAT TGAGCAAA 3180
GTGGTAGCTC TTGGGGGTGA ATTTAAGCTC TACCTGCCCC AGCTGATCCC ACACATGC 3240
CGTGTCTTCA TGCATGACAA CAGCCCAGGC CGCATTGTCT CTATCAAGTT ACTGGCTG 3300
ATCCAGCTGT TTGGCGCCAA CCTGGATGAC TACCTGCATT TACTGCTGCC TCCTATTG 3360
AAGTTGTTTG ATGCCCCTGA AGCTCCACTG CCATCTCGAA AGGCAGCGCT AGAGACTG 3420
GACCGCCTGA CGGAGTCCCT GGATTTCACT GACTATGCCT CCCGGATCAT TCACCCTA 3480
GTTCGAACAC TGGACCAGAG CCCAGAACTG CGCTCCACAG CCATGGACAC GCTGTCTT 3540
CTTGTTTTTC AGCTGGGGAA GAAGTACCAA ATTTTCATTC CAATGGTGAA TAAAGTTC 3600
GTGCGACACC GAATCAATCA TCAGCGCTAT GATGTGCTCA TCTGCAGAAT TGTCAAGG 3660
TACACACTTG CTGATGAAGA GGAGGATCCT TTGATTTACC AGCATCGGAT GCTTAGGA 3720
GGCCAAGGGG ATGCATTGGC TAGTGGACCA GTGGAAACAG GACCCATGAA GAAACTGC 3780
GTCAGCACCA TCAACCTCCA AAAGGCCTGG GGCGCTGCCA GGAGGGTCTC CAAAGATG 3840
TGGCTGGAAT GGCTGAGACG GCTGAGCCTG GAGCTGCTGA AGGACTCATC ATCGCCCT 3900
CTGCGCTCCT GCTGGGCCCT GGCACAGGCC TACAACCCGA TGGCCAGGGA TCTCTTCA 3960
GCTGCATTTG TGTCCTGCTG GTCTGAACTG AATGAAGATC AACAGGATGA GCTCATCA 4020
AGCATCGAGT TGGCCCTCAC CTCACAAGAC ATCGCTGAAG TCACACAGAC CCTCTTAA 4080
TTGGCTGAAT TCATGGAACA CAGTGACAAG GGCCCCCTGC CACTGAGAGA TGACAATG 4140
ATTGTTCTGC TGGGTGAGAG AGCTGCCAAG TGCCGAGCAT ATGCCAAAGC ACTACACT 4200
AAAGAACTGG AGTTCCAGAA AGGCCCCACC CCTGCCATTC TAGAATCTCT CATCAGCA 4260
AATAATAAGC TACAGCAGCC GGAGGCAGCG GCCGGAGTGT TAGAATATGC CATGAAAC 4320
TTTGGAGAGC TGGAGATCCA GGCTACCTGG TATGAGAAAC TGCACGAGTG GGAGGATG 4380
CTTGTGGCCT ATGACAAGAA AATGGACACC AACAAGGACG ACCCAGAGCT GATGCTGG 4440
CGCATGCGCT GCCTCGAGGC CTTGGGGGAA TGGGGTCAAC TCCACCAGCA GTGCTGTG 4500
AAGTGGACCC TGGTTAATGA TGAGACCCAA GCCAAGATGG CCCGGATGGC TGCTGCAG 4560
GCATGGGGTT TAGGTCAGTG GGACAGCATG GAAGAATACA CCTGTATGAT CCCTCGGG 4620
ACCCATGATG GGCATTTTA TAGAGCTGTG CTGGCACTGC ATCAGGACCT CTTCTCCT 4680
GCACAACAGT GCATTGACAA GGCCAGGGAC CTGCTGGATG CTGAATTAAC TGCAATGG 4740
GGAGAGAGTT ACAGTCGGGC ATATGGGCC ATGGTTTCTT GCCACATGCT GTCCGAGC 4800
GAGGAGGTTA TCCAGTACAA ACTTGTCCCC GAGCGACGAG AGATCATCCG CCAGATCT 4860
TGGGAGAGAC TGCAGGGCTG CCAGCGTATC GTAGAGGACT GGCAGAAAAT CCTTATGG 4920
CGGTCCCTTG TGGTCAGCCC TCATGAAGAC ATGAGAACCT GGCTCAAGTA TGCAAGCC 4980
TGCGGCAAGA GTGGCAGGCT GGCTCTTGCT CATAAAACTT TAGTGTTGCT CCTGGGAG 5040
GATCCGTCTC GGCAACTTGA CCATCCTCTG CCAACAGTTC ACCCTCAGGT GACCTATG 5100
TACATGAAAA ACATGTGGAA GAGTGCCCGC AAGATCGATG CCTTCCAGCA CATGCAGC 5160
TTTGTCCAGA CCATGCAGCA ACAGGCCCAG CATGCCATCG CTACTGAGGA CCAGCAGC 5220
AAGCAGGAAC TGCACAAGCT CATGGCCCGA TGCTTCCTGA ACTTGGAGA GTGGCAGC 5280
AATCTACAGG GCATCAATGA GAGCACAATC CCCAAAGTGC TGCAGTACTA CAGCGCCG 5340
```

```
ACAGAGCACG ACCGCAGCTG GTACAAGGCC TGGCATGCGT GGGCAGTGAT GAACTTCG 5400
GCTGTGCTAC ACTACAAACA TCAGAACCAA GCCCGCGATG AGAAGAAGAA ACTGCGTC 5460
GCCAGCGGGG CCAACATCAC CAACGCCACC ACTGCCGCCA CCACGGCCGC CACTGCCA 5520
ACCACTGCCA GCACCGAGGG CAGCAACAGT GAGAGCGAGG CCGAGAGCAC CGAGAACA 5580
CCCACCCCAT CGCCGCTGCA GAAGAAGGTC ACTGAGGATC TGTCCAAAAC CCTCCTGA 5640
TACACGGTGC CTGCCGTCCA GGGCTTCTTC CGTTCCATCT CCTTGTCACG AGGCAACA 5700
CTCCAGGATA CACTCAGAGT TCTCACCTTA TGGTTTGATT ATGGTCACTG GCCAGATG 5760
AATGAGGCCT TAGTGGAGGG GGTGAAAGCC ATCCAGATTG ATACCTGGCT ACAGGTTA 5820
CCTCAGCTCA TTGCAAGAAT TGATACGCCC AGACCCTTGG TGGGACGTCT CATTCACC 5880
CTTCTCACAG ACATTGGTCG GTACCACCCC CAGGCCCTCA TCTACCCACT GACAGTGG 5940
TCTAAGTCTA CCACGACAGC CCGGCACAAT GCAGCCAACA AGATTCTGAA GAACATGT 6000
GAGCACAGCA ACACCCTGGT CCAGCAGGCC ATGATGGTGA GCGAGGAGCT GATCCGAG 6060
GCCATCCTCT GGCATGAGAT GTGGCATGAA GGCCTGGAAG AGGCATCTCG TTTGTACT 6120
GGGGAAAGGA ACGTGAAAGG CATGTTTGAG GTGCTGGAGC CCTTGCATGC TATGATGG 6180
CGGGGCCCCC AGACTCTGAA GGAAACATCC TTTAATCAGG CCTATGGTCG AGATTTAA 6240
GAGGCCCAAG AGTGGTGCAG GAAGTACATG AAATCAGGGA ATGTCAAGGA CCTCACCC 6300
GCCTGGGACC TCTATTATCA TGTGTTCCGA CGAATCTCAA AGCAGCTGCC TCAGCTCA 6360
TCCTTAGAGC TGCAATATGT TTCCCCAAAA CTTCTGATGT GCCGGGACCT TGAATTGG 6420
GTGCCAGGAA CATATGACCC CAACCAGCCA ATCATTCGCA TTCAGTCCAT AGCACCGT 6480
TTGCAAGTCA TCACATCCAA GCAGAGGCCC CGGAAATTGA CACTTATGGG CAGCAACG 6540
CATGAGTTTG TTTTCCTTCT AAAAGGCCAT GAAGATCTGC GCCAGGATGA GCGTGTGA 6600
CAGCTCTTCG GCCTGGTTAA CACCCTTCTG GCCAATGACC AACATCTCT TCGGAAAA 6660
CTCAGCATCC AGAGATACGC TGTCATCCCT TTATCGACCA ACTCGGGCCT CATTGGCT 6720
GTTCCCCACT GTGACACACT GCACGCCCTC ATCCGGGACT ACAGGGAGAA GAAGAAGA 6780
CTTCTCAACA TCGAGCATCG CATCATGTTG CGGATGGCTC CGGACTATGA CCACTTGA 6840
CTGATGCAGA AGGTGGAGGT GTTTGAGCAT GCCGTCAATA ATACAGCTGG GGACGACC 6900
GCCAAGCTGC TGTGGCTGAA AAGCCCCAGC TCCGAGGTGT GGTTTGACCG AAGAACCA 6960
TATACCCGTT CTTTAGCGGT CATGTCAATG GTTGGGTATA TTTTAGGCCT GGGAGATA 7020
CACCCATCCA ACCTGATGCT GGACCGTCTG AGTGGGAAGA TCCTGCACAT TGACTTTG 7080
GACTGCTTTG AGGTTGCTAT GACCCGAGAG AAGTTTCCAG AGAAGATTCC ATTTAGAC 7140
ACAAGAATGT TGACCAATGC TATGGAGGTT ACAGGCCTGG ATGGCAACTA CAGAATCA 7200
TGCCACACAG TGATGGAGGT GCTGCGAGAG CACAAGGACA GTGTCATGGC CGTGCTGG 7260
GCCTTTGTCT ATGACCCCTT GCTGAACTGG AGGCTGATGG ACACAAATAC CAAAGGCA 7320
AAGCGATCCC GAACGAGGAC GGATTCCTAC TCTGCTGGCC AGTCAGTCGA AATTTTGT 7380
GGTGTGGAAC TTGGAGAGCC AGCCCATAAG AAAACGGGGA CCACAGTGCC AGAATCTA 7440
CATTCTTTCA TTGGAGACGG TTTGGTGAAA CCAGAGGCCC TAAATAAGAA AGCTATCC 7500
ATTATTAACA GGGTTCGAGA TAAGCTCACT GGTCGGGACT TCTCTCATGA TGACACTT 7560
GATGTTCCAA CGCAAGTTGA GCTGCTCATC AAACAAGCGA CATCCCATGA AAACCTCT 7620
CAGTGCTATA TTGGCTGGTA CCCTTTCTGG TAA                          7653
```

(2) INFORMATION FOR SEQ ID NO: 2:

(i) SEQUENCE CHARACTERISTICS:
        (A) LENGTH: 3423 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO: 2:

```
ATGTCCCCTA TACTAGGTTA TTGGAAAATT AAGGGCCTTG TGCAACCCAC TCGACTTCTT   60

TTGGAATATC TTGAAGAAAA ATATGAAGAG CATTTGTATG AGCGCGATGA AGGTGATAA   120

TGGCGAAACA AAAAGTTTGA ATTGGGTTTG GAGTTTCCCA ATCTTCCTTA TTATATTGA   180

GGTGATGTTA AATTAACACA GTCTATGGCC ATCATACGTT ATATAGCTGA CAAGCACAA   240

ATGTTGGGTG GTTGTCCAAA AGAGCGTGCA GAGATTTCAA TGCTTGAAGG AGCGGTTTT   300

GATATTAGAT ACGGTGTTTC GAGAATTGCA TATAGTAAAG ACTTTGAAAC TCTCAAAGT   360

GATTTTCTTA GCAAGCTACC TGAAATGCTG AAAATGTTCG AAGATCGTTT ATGTCATAA   420

ACATATTTAA ATGGTGATCA TGTAACCCAT CCTGACTTCA TGTTGTATGA CGCTCTTGA   480

GTTGTTTTAT ACATGGACCC AATGTGCCTG GATGCGTTCC CAAAATTAGT TTGTTTTAA   540

AAACGTATTG AAGCTATCCC ACAAATTGAT AAGTACTTGA ATCCAGCAA GTATATAGC   600

TGGCCTTTGC AGGGCTGGCA AGCCACGTTT GGTGGTGGCG ACCATCCTCC AAAATCGGA   660

CTGGTTCCGC GTGGTGGATC CCGGGAATT TCCGGTGGTG GTGGTGGTGG AATTCTAGA   720

GACTCCATGA GCTTCAAGTA TGCAAGCCTG TGCGGCAAGA GTGGCAGGCT GGCTCTTGC   780

CATAAAACTT TAGTGTTGCT CCTGGGAGTT GATCCGTCTC GGCAACTTGA CCATCCTCT   840

CCAACAGTTC ACCCTCAGGT GACCTATGCC TACATGAAAA ACATGTGGAA GAGTGCCCG   900

AAGATCGATG CCTTCCAGCA CATGCAGCAT TTTGTCCAGA CCATGCAGCA ACAGGCCCA   960

CATGCCATCG CTACTGAGGA CCAGCAGCAT AAGCAGGAAC TGCACAAGCT CATGGCCC  1020

TGCTTCCTGA ACTTGGAGA GTGGCAGCTG AATCTACAGG GCATCAATGA GAGCACAA  1080

CCCAAAGTGC TGCAGTACTA CAGCGCCGCC ACAGAGCACG ACCGCAGCTG GTACAAGG  1140

TGGCATGCGT GGGCAGTGAT GAACTTCGAA GCTGTGCTAC ACTACAAACA TCAGAACC  1200

GCCCGCGATG AGAAGAAGAA ACTGCGTCAT GCCAGCGGGG CCAACATCAC CAACGCCA  1260

ACTGCCGCCA CCACGGCCGC CACTGCCACC ACCACTGCCA GCACCGAGGG CAGCAACA  1320

GAGAGCGAGG CCGAGAGCAC CGAGAACAGC CCCACCCCAT CGCCGCTGCA GAAGAAGG  1380

ACTGAGGATC TGTCCAAAAC CCTCCTGATG TACACGGTGC CTGCCGTCCA GGGCTTCT  1440

CGTTCCATCT CCTTGTCACG AGGCAACAAC CTCCAGGATA CACTCAGAGT TCTCACCT  1500

TGGTTTGATT ATGGTCACTG GCCAGATGTC AATGAGGCCT TAGTGGAGGG GGTGAAAG  1560

ATCCAGATTG ATACCTGGCT ACAGGTTATA CCTCAGCTCA TTGCAAGAAT TGATACGC  1620

AGACCCTTGG TGGGACGTCT CATTCACCAG CTTCTCACAG ACATTGGTCG GTACCACC  1680

CAGGCCCTCA TCTACCCACT GACAGTGGCT TCTAAGTCTA CCACGACAGC CCGGCACA  1740

GCAGCCAACA AGATTCTGAA GAACATGTGT GAGCACAGCA ACACCCTGGT CCAGCAGG  1800

ATGATGGTGA GCGAGGAGCT GATCCGAGTG GCCATCCTCT GGCATGAGAT GTGGCATG  1860

GGCCTGGAAG AGGCATCTCG TTTGTACTTT GGGGAAAGGA ACGTGAAAGG CATGTTTG  1920

GTGCTGGAGC CCTTGCATGC TATGATGGAA CGGGGCCCCC AGACTCTGAA GGAAACAT  1980
```

```
TTTAATCAGG CCTATGGTCG AGATTTAATG GAGGCCCAAG AGTGGTGCAG GAAGTACA  2040
AAATCAGGGA ATGTCAAGGA CCTCACCCAA GCCTGGGACC TCTATTATCA TGTGTTCC  2100
CGAATCTCAA AGCAGCTGCC TCAGCTCACA TCCTTAGAGC TGCAATATGT TTCCCCAA  2160
CTTCTGATGT GCCGGGACCT TGAATTGGCT GTGCCAGGAA CATATGACCC CAACCAGC  2220
ATCATTCGCA TTCAGTCCAT AGCACCGTCT TTGCAAGTCA TCACATCCAA GCAGAGGC  2280
CGGAAATTGA CACTTATGGG CAGCAACGGA CATGAGTTTG TTTTCCTTCT AAAAGGCC  2340
GAAGATCTGC GCCAGGATGA GCGTGTGATG CAGCTCTTCG GCCTGGTTAA CACCCTTC  2400
GCCAATGACC CAACATCTCT TCGGAAAAAC CTCAGCATCC AGAGATACGC TGTCATCC  2460
TTATCGACCA ACTCGGGCCT CATTGGCTGG GTTCCCCACT GTGACACACT GCACGCCC  2520
ATCCGGGACT ACAGGGAGAA GAAGAAGATC CTTCTCAACA TCGAGCATCG CATCATGT  2580
CGGATGGCTC CGGACTATGA CCACTTGACT CTGATGCAGA AGGTGGAGGT GTTTGAGC  2640
GCCGTCAATA ATACAGCTGG GGACGACCTG GCCAAGCTGC TGTGGCTGAA AAGCCCCA  2700
TCCGAGGTGT GGTTTGACCG AAGAACCAAT TATACCCGTT CTTTAGCGGT CATGTCAA  2760
GTTGGGTATA TTTTAGGCCT GGGAGATAGA CACCCATCCA ACCTGATGCT GGACCGTC  2820
AGTGGGAAGA TCCTGCACAT TGACTTTGGG GACTGCTTTG AGGTTGCTAT GACCCGAG  2880
AAGTTTCCAG AGAAGATTCC ATTTAGACTA ACAAGAATGT TGACCAATGC TATGGAGG  2940
ACAGGCCTGG ATGGCAACTA CAGAATCACA TGCCACACAG TGATGGAGGT GCTGCGAG  3000
CACAAGGACA GTGTCATGGC CGTGCTGGAA GCCTTTGTCT ATGACCCCTT GCTGAACT  3060
AGGCTGATGG ACACAAATAC CAAAGGCAAC AAGCGATCCC GAACGAGGAC GGATTCCT  3120
TCTGCTGGCC AGTCAGTCGA AATTTTGGAC GGTGTGGAAC TTGGAGAGCC AGCCCATA  3180
AAAACGGGGA CCACAGTGCC AGAATCTATT CATTCTTTCA TTGGAGACGG TTTGGTGA  3240
CCAGAGGCCC TAAATAAGAA AGCTATCCAG ATTATTAACA GGGTTCGAGA TAAGCTCA  3300
GGTCGGGACT TCTCTCATGA TGACACTTTG GATGTTCCAA CGCAAGTTGA GCTGCTCA  3360
AAACAAGCGA CATCCCATGA AAACCTCTGC CAGTGCTATA TTGGCTGGTA CCCTTTCT  3420
TAA                                                             3423
```

(2) INFORMATION FOR SEQ ID NO: 3:

(i) SEQUENCE CHARACTERISTICS:
        (A) LENGTH: 2549 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

```
Met Leu Gly Thr Gly Pro Ala Ala Thr Thr Ala Ala Thr Thr Se
 1               5                  10                  15

Ser Asn Val Ser Val Leu Gln Gln Phe Ala Ser Gly Leu Lys Ser Ar
                20                  25                  30

Asn Glu Glu Thr Arg Ala Lys Ala Ala Lys Glu Leu Gln His Tyr Va
            35                  40                  45

Thr Met Glu Leu Arg Glu Met Ser Gln Glu Glu Ser Thr Arg Phe Ty
        50                  55                  60

Asp Gln Leu Asn His His Ile Phe Glu Leu Val Ser Ser Ser Asp Al
65                  70                  75                  80

Asn Glu Arg Lys Gly Gly Ile Leu Ala Ile Ala Ser Leu Ile Gly Va
```

```
                   85                  90                  95
Glu Gly Gly Asn Ala Thr Arg Ile Gly Arg Phe Ala Asn Tyr Leu Ar
                100                 105                 110
Asn Leu Leu Pro Ser Asn Asp Pro Val Val Met Glu Met Ala Ser Ly
            115                 120                 125
Ala Ile Gly Arg Leu Ala Met Ala Gly Asp Thr Phe Thr Ala Glu Ty
        130                 135                 140
Val Glu Phe Glu Val Lys Arg Ala Leu Glu Trp Leu Gly Ala Asp Ar
145                 150                 155                 160
Asn Glu Gly Arg Arg His Ala Ala Val Leu Val Leu Arg Glu Leu Al
                165                 170                 175
Ile Ser Val Pro Thr Phe Phe Gln Gln Val Gln Pro Phe Phe As
            180                 185                 190
Asn Ile Phe Val Ala Val Trp Asp Pro Lys Gln Ala Ile Arg Glu Gl
        195                 200                 205
Ala Val Ala Ala Leu Arg Ala Cys Leu Ile Leu Thr Thr Gln Arg Gl
    210                 215                 220
Pro Lys Glu Met Gln Lys Pro Gln Trp Tyr Arg His Thr Phe Glu Gl
225                 230                 235                 240
Ala Glu Lys Gly Phe Asp Glu Thr Leu Ala Lys Glu Lys Gly Met As
                245                 250                 255
Arg Asp Asp Arg Ile His Gly Ala Leu Leu Ile Leu Asn Glu Leu Va
            260                 265                 270
Arg Ile Ser Ser Met Glu Gly Glu Arg Leu Arg Glu Met Glu Gl
        275                 280                 285
Ile Thr Gln Gln Gln Leu Val His Asp Lys Tyr Cys Lys Asp Leu Me
    290                 295                 300
Gly Phe Gly Thr Lys Pro Arg His Ile Thr Pro Phe Thr Ser Phe Gl
305                 310                 315                 320
Ala Val Gln Pro Gln Gln Ser Asn Ala Leu Val Gly Leu Leu Gly Ty
                325                 330                 335
Ser Ser His Gln Gly Leu Met Gly Phe Gly Thr Ser Pro Ser Pro Al
            340                 345                 350
Lys Ser Thr Leu Val Glu Ser Arg Cys Cys Arg Asp Leu Met Glu Gl
        355                 360                 365
Lys Phe Asp Gln Val Cys Gln Trp Val Leu Lys Cys Arg Asn Ser Ly
    370                 375                 380
Asn Ser Leu Ile Gln Met Thr Ile Leu Asn Leu Pro Arg Leu Al
385                 390                 395                 400
Ala Phe Arg Pro Ser Ala Phe Thr Asp Thr Gln Tyr Leu Gln Asp Th
                405                 410                 415
Met Asn His Ala Leu Ser Cys Val Lys Lys Glu Lys Arg Thr Al
            420                 425                 430
Ala Phe Gln Ala Leu Gly Leu Leu Ser Val Ala Val Arg Ser Glu Ph
        435                 440                 445
Lys Val Tyr Leu Pro Arg Val Leu Asp Ile Ile Arg Ala Ala Leu Pr
    450                 455                 460
Pro Lys Asp Phe Ala His Lys Arg Gln Lys Ala Met Gln Val Asp Al
465                 470                 475                 480
Thr Val Phe Thr Cys Ile Ser Met Leu Ala Arg Ala Met Gly Pro Gl
                485                 490                 495
Ile Gln Gln Asp Ile Lys Glu Leu Leu Glu Pro Met Leu Ala Val Gl
            500                 505                 510
```

```
Leu Ser Pro Ala Leu Thr Ala Val Leu Tyr Asp Leu Ser Arg Gln Il
            515                 520                 525
Pro Gln Leu Lys Lys Asp Ile Gln Asp Gly Leu Leu Lys Met Leu Se
        530                 535                 540
Leu Val Leu Met His Lys Pro Leu Arg His Pro Gly Met Pro Lys Gl
545                 550                 555                 560
Leu Ala His Gln Leu Ala Ser Pro Gly Leu Thr Thr Leu Pro Glu Al
                565                 570                 575
Ser Asp Val Gly Ser Ile Thr Leu Ala Leu Arg Thr Leu Gly Ser Ph
            580                 585                 590
Glu Phe Glu Gly His Ser Leu Thr Gln Phe Val Arg His Cys Ala As
        595                 600                 605
His Phe Leu Asn Ser Glu His Lys Glu Ile Arg Met Glu Ala Ala Ar
    610                 615                 620
Thr Cys Ser Arg Leu Leu Thr Pro Ser Ile His Leu Ile Ser Gly Hi
625                 630                 635                 640
Ala His Val Val Ser Gln Thr Ala Val Gln Val Val Ala Asp Val Le
                645                 650                 655
Ser Lys Leu Leu Val Val Gly Ile Thr Asp Pro Asp Pro Asp Ile Ar
            660                 665                 670
Tyr Cys Val Leu Ala Ser Leu Asp Glu Arg Phe Asp Ala His Leu Al
        675                 680                 685
Gln Ala Glu Asn Leu Gln Ala Leu Phe Val Ala Leu Asn Asp Gln Va
    690                 695                 700
Phe Glu Ile Arg Glu Leu Ala Ile Cys Thr Val Gly Arg Leu Ser Se
705                 710                 715                 720
Met Asn Pro Ala Phe Val Met Pro Phe Leu Arg Lys Met Leu Ile Gl
                725                 730                 735
Ile Leu Thr Glu Leu Glu His Ser Gly Ile Gly Arg Ile Lys Glu Gl
            740                 745                 750
Ser Ala Arg Met Leu Gly His Leu Val Ser Asn Ala Pro Arg Leu Il
        755                 760                 765
Arg Pro Tyr Met Glu Pro Ile Leu Lys Ala Leu Ile Leu Lys Leu Ly
    770                 775                 780
Asp Pro Asp Pro Asp Pro Asn Pro Gly Val Ile Asn Asn Val Leu Al
785                 790                 795                 800
Thr Ile Gly Glu Leu Ala Gln Val Ser Gly Leu Glu Met Arg Lys Tr
                805                 810                 815
Val Asp Glu Leu Phe Ile Ile Met Asp Met Leu Gln Asp Ser Se
            820                 825                 830
Leu Leu Ala Lys Arg Gln Val Ala Leu Trp Thr Leu Gly Gln Leu Va
        835                 840                 845
Ala Ser Thr Gly Tyr Val Val Glu Pro Tyr Arg Lys Tyr Pro Thr Le
    850                 855                 860
Leu Glu Val Leu Leu Asn Phe Leu Lys Thr Glu Gln Asn Gln Gly Th
865                 870                 875                 880
Arg Arg Glu Ala Ile Arg Val Leu Gly Leu Leu Gly Ala Leu Asp Pr
                885                 890                 895
Tyr Lys His Lys Val Asn Ile Gly Met Ile Asp Gln Ser Arg Asp Al
            900                 905                 910
Ser Ala Val Ser Leu Ser Glu Ser Lys Ser Ser Gln Asp Ser Ser As
        915                 920                 925
```

-continued

```
Tyr Ser Thr Ser Glu Met Leu Val Asn Met Gly Asn Leu Pro Leu As
    930                 935                 940
Glu Phe Tyr Pro Ala Val Ser Met Val Ala Leu Met Arg Ile Phe Ar
945                 950                 955                 960
Asp Gln Ser Leu Ser His His Thr Met Val Gln Ala Ile Th
                965                 970                 975
Phe Ile Phe Lys Ser Leu Gly Leu Lys Cys Val Gln Phe Leu Pro Gl
                980                 985                 990
Val Met Pro Thr Phe Leu Asn Val Ile Arg Val Cys Asp Gly Ala Il
            995                 1000                1005
Arg Glu Phe Leu Phe Gln Gln Leu Gly Met Leu Val Ser Phe Val Ly
        1010                1015                1020
Ser His Ile Arg Pro Tyr Met Asp Glu Ile Val Thr Leu Met Arg Gl
1025                1030                1035                1040
Phe Trp Val Met Asn Thr Ser Ile Gln Ser Thr Ile Ile Leu Leu Il
                1045                1050                1055
Glu Gln Ile Val Val Ala Leu Gly Gly Glu Phe Lys Leu Tyr Leu Pr
                1060                1065                1070
Gln Leu Ile Pro His Met Leu Arg Val Phe Met His Asp Asn Ser Pr
        1075                1080                1085
Gly Arg Ile Val Ser Ile Lys Leu Leu Ala Ala Ile Gln Leu Phe Gl
1090                1095                1100
Ala Asn Leu Asp Asp Tyr Leu His Leu Leu Pro Pro Ile Val Ly
1105                1110                1115                1120
Leu Phe Asp Ala Pro Glu Ala Pro Leu Pro Ser Arg Lys Ala Ala Le
                1125                1130                1135
Glu Thr Val Asp Arg Leu Thr Glu Ser Leu Asp Phe Thr Asp Tyr Al
                1140                1145                1150
Ser Arg Ile Ile His Pro Ile Val Arg Thr Leu Asp Gln Ser Pro Gl
            1155                1160                1165
Leu Arg Ser Thr Ala Met Asp Thr Leu Ser Ser Leu Val Phe Gln Le
        1170                1175                1180
Gly Lys Lys Tyr Gln Ile Phe Ile Pro Met Val Asn Lys Val Leu Va
1185                1190                1195                1200
Arg His Arg Ile Asn His Gln Arg Tyr Asp Val Leu Ile Cys Arg Il
                1205                1210                1215
Val Lys Gly Tyr Thr Leu Ala Asp Glu Glu Asp Pro Leu Ile Ty
            1220                1225                1230
Gln His Arg Met Leu Arg Ser Gly Gln Gly Asp Ala Leu Ala Ser Gl
        1235                1240                1245
Pro Val Glu Thr Gly Pro Met Lys Lys Leu His Val Ser Thr Ile As
    1250                1255                1260
Leu Gln Lys Ala Trp Gly Ala Ala Arg Arg Val Ser Lys Asp Asp Tr
1265                1270                1275                1280
Leu Glu Trp Leu Arg Arg Leu Ser Leu Glu Leu Leu Lys Asp Ser Se
                1285                1290                1295
Ser Pro Ser Leu Arg Ser Cys Trp Ala Leu Ala Gln Ala Tyr Asn Pr
        1300                1305                1310
Met Ala Arg Asp Leu Phe Asn Ala Ala Phe Val Ser Cys Trp Ser Gl
    1315                1320                1325
Leu Asn Glu Asp Gln Gln Asp Glu Leu Ile Arg Ser Ile Glu Leu Al
    1330                1335                1340
Leu Thr Ser Gln Asp Ile Ala Glu Val Thr Gln Thr Leu Leu Asn Le
```

```
                1345                1350                1355                1360
         Ala Glu Phe Met Glu His Ser Asp Lys Gly Pro Leu Pro Leu Arg As
                          1365                1370                1375

Asp Asn Gly Ile Val Leu Leu Gly Glu Arg Ala Ala Lys Cys Arg Al
                 1380                1385                1390

Tyr Ala Lys Ala Leu His Tyr Lys Glu Leu Glu Phe Gln Lys Gly Pr
                 1395                1400                1405

Thr Pro Ala Ile Leu Glu Ser Leu Ile Ser Ile Asn Asn Lys Leu Gl
                 1410                1415                1420

Gln Pro Glu Ala Ala Ala Gly Val Leu Glu Tyr Ala Met Lys His Ph
         1425                1430                1435                1440

Gly Glu Leu Glu Ile Gln Ala Thr Trp Tyr Glu Lys Leu His Glu Tr
                       1445                1450                1455

Glu Asp Ala Leu Val Ala Tyr Asp Lys Lys Met Asp Thr Asn Lys As
                 1460                1465                1470

Asp Pro Glu Leu Met Leu Gly Arg Met Arg Cys Leu Glu Ala Leu Gl
                 1475                1480                1485

Glu Trp Gly Gln Leu His Gln Gln Cys Cys Glu Lys Trp Thr Leu Va
                 1490                1495                1500

Asn Asp Glu Thr Gln Ala Lys Met Ala Arg Met Ala Ala Ala Al
         1505                1510                1515                1520

Trp Gly Leu Gly Gln Trp Asp Ser Met Glu Glu Tyr Thr Cys Met Il
                       1525                1530                1535

Pro Arg Asp Thr His Asp Gly Ala Phe Tyr Arg Ala Val Leu Ala Le
                 1540                1545                1550

His Gln Asp Leu Phe Ser Leu Ala Gln Gln Cys Ile Asp Lys Ala Ar
                 1555                1560                1565

Asp Leu Leu Asp Ala Glu Leu Thr Ala Met Ala Gly Glu Ser Tyr Se
                 1570                1575                1580

Arg Ala Tyr Gly Ala Met Val Ser Cys His Met Leu Ser Glu Leu Gl
         1585                1590                1595                1600

Glu Val Ile Gln Tyr Lys Leu Val Pro Glu Arg Arg Glu Ile Ile Ar
                       1605                1610                1615

Gln Ile Trp Trp Glu Arg Leu Gln Gly Cys Gln Arg Ile Val Glu As
                 1620                1625                1630

Trp Gln Lys Ile Leu Met Val Arg Ser Leu Val Val Ser Pro His Gl
                 1635                1640                1645

Asp Met Arg Thr Trp Leu Lys Tyr Ala Ser Leu Cys Gly Lys Ser Gl
                 1650                1655                1660

Arg Leu Ala Leu Ala His Lys Thr Leu Val Leu Leu Leu Gly Val As
         1665                1670                1675                1680

Pro Ser Arg Gln Leu Asp His Pro Leu Pro Thr Val His Pro Gln Va
                       1685                1690                1695

Thr Tyr Ala Tyr Met Lys Asn Met Trp Lys Ser Ala Arg Lys Ile As
                 1700                1705                1710

Ala Phe Gln His Met Gln His Phe Val Gln Thr Met Gln Gln Al
                 1715                1720                1725

Gln His Ala Ile Ala Thr Glu Asp Gln Gln His Lys Gln Glu Leu Hi
                 1730                1735                1740

Lys Leu Met Ala Arg Cys Phe Leu Lys Leu Gly Glu Trp Gln Leu As
         1745                1750                1755                1760

Leu Gln Gly Ile Asn Glu Ser Thr Ile Pro Lys Val Leu Gln Tyr Ty
                       1765                1770                1775
```

```
Ser Ala Ala Thr Glu His Asp Arg Ser Trp Tyr Lys Ala Trp His Al
             1780                1785                1790
Trp Ala Val Met Asn Phe Glu Ala Val Leu His Tyr Lys His Gln As
         1795                1800                1805
Gln Ala Arg Asp Glu Lys Lys Lys Leu Arg His Ala Ser Gly Ala As
     1810                1815                1820
Ile Thr Asn Ala Thr Thr Ala Ala Thr Ala Ala Thr Ala Thr Th
1825                1830                1835                1840
Thr Ala Ser Thr Glu Gly Ser Asn Ser Glu Ser Glu Ala Glu Ser Th
                 1845                1850                1855
Glu Asn Ser Pro Thr Pro Ser Pro Leu Gln Lys Lys Val Thr Glu As
             1860                1865                1870
Leu Ser Lys Thr Leu Leu Met Tyr Thr Val Pro Ala Val Gln Gly Ph
         1875                1880                1885
Phe Arg Ser Ile Ser Leu Ser Arg Gly Asn Asn Leu Gln Asp Thr Le
     1890                1895                1900
Arg Val Leu Thr Leu Trp Phe Asp Tyr Gly His Trp Pro Asp Val As
1905                1910                1915                1920
Glu Ala Leu Val Glu Gly Val Lys Ala Ile Gln Ile Asp Thr Trp Le
                 1925                1930                1935
Gln Val Ile Pro Gln Leu Ile Ala Arg Ile Asp Thr Pro Arg Pro Le
             1940                1945                1950
Val Gly Arg Leu Ile His Gln Leu Leu Thr Asp Ile Gly Arg Tyr Hi
         1955                1960                1965
Pro Gln Ala Leu Ile Tyr Pro Leu Thr Val Ala Ser Lys Ser Thr Th
     1970                1975                1980
Thr Ala Arg His Asn Ala Ala Asn Lys Ile Leu Lys Asn Met Cys Gl
1985                1990                1995                2000
His Ser Asn Thr Leu Val Gln Gln Ala Met Met Val Ser Glu Glu Le
                 2005                2010                2015
Ile Arg Val Ala Ile Leu Trp His Glu Met Trp His Glu Gly Leu Gl
             2020                2025                2030
Glu Ala Ser Arg Leu Tyr Phe Gly Glu Arg Asn Val Lys Gly Met Ph
         2035                2040                2045
Glu Val Leu Glu Pro Leu His Ala Met Met Glu Arg Gly Pro Gln Th
     2050                2055                2060
Leu Lys Glu Thr Ser Phe Asn Gln Ala Tyr Gly Arg Asp Leu Met Gl
2065                2070                2075                2080
Ala Gln Glu Trp Cys Arg Lys Tyr Met Lys Ser Gly Asn Val Lys As
                 2085                2090                2095
Leu Thr Gln Ala Trp Asp Leu Tyr Tyr His Val Phe Arg Arg Ile Se
             2100                2105                2110
Lys Gln Leu Pro Gln Leu Thr Ser Leu Glu Leu Gln Tyr Val Ser Pr
         2115                2120                2125
Lys Leu Leu Met Cys Arg Asp Leu Glu Leu Ala Val Pro Gly Thr Ty
     2130                2135                2140
Asp Pro Asn Gln Pro Ile Ile Arg Ile Gln Ser Ile Ala Pro Ser Le
2145                2150                2155                2160
Gln Val Ile Thr Ser Lys Gln Arg Pro Arg Lys Leu Thr Leu Met Gl
                 2165                2170                2175
Ser Asn Gly His Glu Phe Val Phe Leu Leu Lys Gly His Glu Asp Le
             2180                2185                2190
```

```
Arg Gln Asp Glu Arg Val Met Gln Leu Phe Gly Leu Val Asn Thr Le
        2195                2200                2205

Leu Ala Asn Asp Pro Thr Ser Leu Arg Lys Asn Leu Ser Ile Gln Ar
    2210                2215                2220

Tyr Ala Val Ile Pro Leu Ser Thr Asn Ser Gly Leu Ile Gly Trp Va
2225                2230                2235                2240

Pro His Cys Asp Thr Leu His Ala Leu Ile Arg Asp Tyr Arg Glu Ly
            2245                2250                2255

Lys Lys Ile Leu Leu Asn Ile Glu His Arg Ile Met Leu Arg Met Al
            2260                2265                2270

Pro Asp Tyr Asp His Leu Thr Leu Met Gln Lys Val Glu Val Phe Gl
            2275                2280                2285

His Ala Val Asn Asn Thr Ala Gly Asp Asp Leu Ala Lys Leu Leu Tr
        2290                2295                2300

Leu Lys Ser Pro Ser Ser Glu Val Trp Phe Asp Arg Arg Thr Asn Ty
2305                2310                2315                2320

Thr Arg Ser Leu Ala Val Met Ser Met Val Gly Tyr Ile Leu Gly Le
                2325                2330                2335

Gly Asp Arg His Pro Ser Asn Leu Met Leu Asp Arg Leu Ser Gly Ly
                2340                2345                2350

Ile Leu His Ile Asp Phe Gly Asp Cys Phe Glu Val Ala Met Thr Ar
        2355                2360                2365

Glu Lys Phe Pro Glu Lys Ile Pro Phe Arg Leu Thr Arg Met Leu Th
    2370                2375                2380

Asn Ala Met Glu Val Thr Gly Leu Asp Gly Asn Tyr Arg Ile Thr Cy
2385                2390                2395                2400

His Thr Val Met Glu Val Leu Arg Glu His Lys Asp Ser Val Met Al
                2405                2410                2415

Val Leu Glu Ala Phe Val Tyr Asp Pro Leu Leu Asn Trp Arg Leu Me
                2420                2425                2430

Asp Thr Asn Thr Lys Gly Asn Lys Arg Ser Arg Thr Arg Thr Asp Se
            2435                2440                2445

Tyr Ser Ala Gly Gln Ser Val Glu Ile Leu Asp Gly Val Glu Leu Gl
    2450                2455                2460

Glu Pro Ala His Lys Lys Thr Gly Thr Thr Val Pro Glu Ser Ile Hi
2465                2470                2475                2480

Ser Phe Ile Gly Asp Gly Leu Val Lys Pro Glu Ala Leu Asn Lys Ly
                2485                2490                2495

Ala Ile Gln Ile Ile Asn Arg Val Arg Asp Lys Leu Thr Gly Arg As
            2500                2505                2510

Phe Ser His Asp Asp Thr Leu Asp Val Pro Thr Gln Val Glu Leu Le
        2515                2520                2525

Ile Lys Gln Ala Thr Ser His Glu Asn Leu Cys Gln Cys Tyr Ile Gl
    2530                2535                2540

Trp Tyr Pro Phe Trp
2545
```

(2) INFORMATION FOR SEQ ID NO: 4:

(i) SEQUENCE CHARACTERISTICS:
      (A) LENGTH: 1140 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 4:

Met Ser Pro Ile Leu Gly Tyr Trp Lys Ile Lys Gly Leu Val Gln Pr
1               5                   10                  15

Thr Arg Leu Leu Leu Glu Tyr Leu Glu Glu Lys Tyr Glu Glu His Le
            20                  25                  30

Tyr Glu Arg Asp Glu Gly Asp Lys Trp Arg Asn Lys Lys Phe Glu Le
        35                  40                  45

Gly Leu Glu Phe Pro Asn Leu Pro Tyr Tyr Ile Asp Gly Asp Val Ly
    50                  55                  60

Leu Thr Gln Ser Met Ala Ile Ile Arg Tyr Ile Ala Asp Lys His As
65              70                  75                      80

Met Leu Gly Gly Cys Pro Lys Glu Arg Ala Glu Ile Ser Met Leu Gl
                85                  90                  95

Gly Ala Val Leu Asp Ile Arg Tyr Gly Val Ser Arg Ile Ala Tyr Se
            100                 105                 110

Lys Asp Phe Glu Thr Leu Lys Val Asp Phe Leu Ser Lys Leu Pro Gl
        115                 120                 125

Met Leu Lys Met Phe Glu Asp Arg Leu Cys His Lys Thr Tyr Leu As
130                 135                 140

Gly Asp His Val Thr His Pro Asp Phe Met Leu Tyr Asp Ala Leu As
145                 150                 155                 160

Val Val Leu Tyr Met Asp Pro Met Cys Leu Asp Ala Phe Pro Lys Le
                165                 170                 175

Val Cys Phe Lys Lys Arg Ile Glu Ala Ile Pro Gln Ile Asp Lys Ty
            180                 185                 190

Leu Lys Ser Ser Lys Tyr Ile Ala Trp Pro Leu Gln Gly Trp Gln Al
        195                 200                 205

Thr Phe Gly Gly Gly Asp His Pro Pro Lys Ser Asp Leu Val Pro Ar
    210                 215                 220

Gly Gly Ser Pro Gly Ile Ser Gly Gly Gly Gly Gly Ile Leu As
225                 230                 235                 240

Asp Ser Met Ser Phe Lys Tyr Ala Ser Leu Cys Gly Lys Ser Gly Ar
                245                 250                 255

Leu Ala Leu Ala His Lys Thr Leu Val Leu Leu Leu Gly Val Asp Pr
            260                 265                 270

Ser Arg Gln Leu Asp His Pro Leu Pro Thr Val His Pro Gln Val Th
        275                 280                 285

Tyr Ala Tyr Met Lys Asn Met Trp Lys Ser Ala Arg Lys Ile Asp Al
    290                 295                 300

Phe Gln His Met Gln His Phe Val Gln Thr Met Gln Gln Ala Gl
305                 310                 315                 320

His Ala Ile Ala Thr Glu Asp Gln Gln His Lys Gln Glu Leu His Ly
                325                 330                 335

Leu Met Ala Arg Cys Phe Leu Lys Leu Gly Glu Trp Gln Leu Asn Le
            340                 345                 350

Gln Gly Ile Asn Glu Ser Thr Ile Pro Lys Val Leu Gln Tyr Tyr Se
        355                 360                 365

Ala Ala Thr Glu His Asp Arg Ser Trp Tyr Lys Ala Trp His Ala Tr
    370                 375                 380

Ala Val Met Asn Phe Glu Ala Val Leu His Tyr Lys His Gln Asn Gl
385                 390                 395                 400

Ala Arg Asp Glu Lys Lys Lys Leu Arg His Ala Ser Gly Ala Asn Il

-continued

```
                405                 410                 415
Thr Asn Ala Thr Thr Ala Ala Thr Thr Ala Thr Ala Thr Thr Th
                420                 425                 430
Ala Ser Thr Glu Gly Ser Asn Ser Glu Ser Ala Glu Ser Thr Gl
                435                 440                 445
Asn Ser Pro Thr Pro Ser Pro Leu Gln Lys Lys Val Thr Glu Asp Le
                450                 455                 460
Ser Lys Thr Leu Leu Met Tyr Thr Val Pro Ala Val Gln Gly Phe Ph
465                 470                 475                 480
Arg Ser Ile Ser Leu Ser Arg Gly Asn Asn Leu Gln Asp Thr Leu Ar
                485                 490                 495
Val Leu Thr Leu Trp Phe Asp Tyr Gly His Trp Pro Asp Val Asn Gl
                500                 505                 510
Ala Leu Val Glu Gly Val Lys Ala Ile Gln Ile Asp Thr Trp Leu Gl
                515                 520                 525
Val Ile Pro Gln Leu Ile Ala Arg Ile Asp Thr Pro Arg Pro Leu Va
                530                 535                 540
Gly Arg Leu Ile His Gln Leu Leu Thr Asp Ile Gly Arg Tyr His Pr
545                 550                 555                 560
Gln Ala Leu Ile Tyr Pro Leu Thr Val Ala Ser Lys Ser Thr Thr Th
                565                 570                 575
Ala Arg His Asn Ala Ala Asn Lys Ile Leu Lys Asn Met Cys Glu Hi
                580                 585                 590
Ser Asn Thr Leu Val Gln Gln Ala Met Met Val Ser Glu Glu Leu Il
                595                 600                 605
Arg Val Ala Ile Leu Trp His Glu Met Trp His Glu Gly Leu Glu Gl
                610                 615                 620
Ala Ser Arg Leu Tyr Phe Gly Glu Arg Asn Val Lys Gly Met Phe Gl
625                 630                 635                 640
Val Leu Glu Pro Leu His Ala Met Met Glu Arg Gly Pro Gln Thr Le
                645                 650                 655
Lys Glu Thr Ser Phe Asn Gln Ala Tyr Gly Arg Asp Leu Met Glu Al
                660                 665                 670
Gln Glu Trp Cys Arg Lys Tyr Met Lys Ser Gly Asn Val Lys Asp Le
                675                 680                 685
Thr Gln Ala Trp Asp Leu Tyr Tyr His Val Phe Arg Arg Ile Ser Ly
                690                 695                 700
Gln Leu Pro Gln Leu Thr Ser Leu Glu Leu Gln Tyr Val Ser Pro Ly
705                 710                 715                 720
Leu Leu Met Cys Arg Asp Leu Glu Leu Ala Val Pro Gly Thr Tyr As
                725                 730                 735
Pro Asn Gln Pro Ile Ile Arg Ile Gln Ser Ile Ala Pro Ser Leu Gl
                740                 745                 750
Val Ile Thr Ser Lys Gln Arg Pro Arg Lys Leu Thr Leu Met Gly Se
                755                 760                 765
Asn Gly His Glu Phe Val Phe Leu Leu Lys Gly His Glu Asp Leu Ar
                770                 775                 780
Gln Asp Glu Arg Val Met Gln Leu Phe Gly Leu Val Asn Thr Leu Le
785                 790                 795                 800
Ala Asn Asp Pro Thr Ser Leu Arg Lys Asn Leu Ser Ile Gln Arg Ty
                805                 810                 815
Ala Val Ile Pro Leu Ser Thr Asn Ser Gly Leu Ile Gly Trp Val Pr
                820                 825                 830
```

```
His Cys Asp Thr Leu His Ala Leu Ile Arg Asp Tyr Arg Glu Lys Ly
        835                 840                 845
Lys Ile Leu Leu Asn Ile Glu His Arg Ile Met Leu Arg Met Ala Pr
        850                 855                 860
Asp Tyr Asp His Leu Thr Leu Met Gln Lys Val Glu Val Phe Glu Hi
865                 870                 875                 880
Ala Val Asn Asn Thr Ala Gly Asp Asp Leu Ala Lys Leu Leu Trp Le
                885                 890                 895
Lys Ser Pro Ser Ser Glu Val Trp Phe Asp Arg Arg Thr Asn Tyr Th
                900                 905                 910
Arg Ser Leu Ala Val Met Ser Met Val Gly Tyr Ile Leu Gly Leu Gl
        915                 920                 925
Asp Arg His Pro Ser Asn Leu Met Leu Asp Arg Leu Ser Gly Lys Il
930                 935                 940
Leu His Ile Asp Phe Gly Asp Cys Phe Glu Val Ala Met Thr Arg Gl
945                 950                 955                 960
Lys Phe Pro Glu Lys Ile Pro Phe Arg Leu Thr Arg Met Leu Thr As
                965                 970                 975
Ala Met Glu Val Thr Gly Leu Asp Gly Asn Tyr Arg Ile Thr Cys Hi
        980                 985                 990
Thr Val Met Glu Val Leu Arg Glu His Lys Asp Ser Val Met Ala Va
        995                 1000                1005
Leu Glu Ala Phe Val Tyr Asp Pro Leu Leu Asn Trp Arg Leu Met As
        1010                1015                1020
Thr Asn Thr Lys Gly Asn Lys Arg Ser Arg Thr Arg Thr Asp Ser Ty
1025                1030                1035                1040
Ser Ala Gly Gln Ser Val Glu Ile Leu Asp Gly Val Glu Leu Gly Gl
                1045                1050                1055
Pro Ala His Lys Lys Thr Gly Thr Thr Val Pro Glu Ser Ile His Se
        1060                1065                1070
Phe Ile Gly Asp Gly Leu Val Lys Pro Glu Ala Leu Asn Lys Lys Al
        1075                1080                1085
Ile Gln Ile Ile Asn Arg Val Arg Asp Lys Leu Thr Gly Arg Asp Ph
        1090                1095                1100
Ser His Asp Asp Thr Leu Asp Val Pro Thr Gln Val Glu Leu Leu Il
1105                1110                1115                1120
Lys Gln Ala Thr Ser His Glu Asn Leu Cys Gln Cys Tyr Ile Gly Tr
                1125                1130                1135
Tyr Pro Phe Trp
                1140
```

(2) INFORMATION FOR SEQ ID NO: 5:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 5:

```
Ile Leu Leu Asn Ile Glu His Arg
1               5
```

(2) INFORMATION FOR SEQ ID NO: 6:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

Leu Ile Arg Pro Tyr Met Glu Pro Ile Leu Lys
        1               5                   10

(2) INFORMATION FOR SEQ ID NO: 7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

Asp Xaa Met Glu Ala Gln Glu
        1               5

(2) INFORMATION FOR SEQ ID NO: 8:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

Gln Leu Asp His Pro Leu Pro Thr Val His Pro Gln Val Thr Tyr Al
        1               5                   10                  15

Tyr Met Lys (2) INFORMATION FOR SEQ ID NO: 9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CGATCGGTCG ACTGCAGCAC TTTGGGGATT GTGCTCTC                                38

(2) INFORMATION FOR SEQ ID NO: 10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

GCGGCCGCAG CTTTCTTCAT GCATGACAAC AGCCCAGGC                               39

(2) INFORMATION FOR SEQ ID NO: 11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

GCGGCCGCAA GCTTCAAGTA TGCAAGCCTG TGCGGCAAGA                40

(2) INFORMATION FOR SEQ ID NO: 12:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

CGATCGGTCG ACACCTTCTG CATCAGAGTC AAGTGGTCA                39

(2) INFORMATION FOR SEQ ID NO: 13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

GCGGCCGCAA GCTTCCTCAG CTCACATCCT TAGAGCTGCA                40

(2) INFORMATION FOR SEQ ID NO: 14:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

CGATCGGTCG ACTTATTACC AGAAAGGGCA CCAGCCAATA TA             42

(2) INFORMATION FOR SEQ ID NO: 15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

CGATCGGTCG ACCAGATGAG CACATCATAG CGCTGATGA                39

(2) INFORMATION FOR SEQ ID NO: 16:

(i) SEQUENCE CHARACTERISTICS:
        (A) LENGTH: 39 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

CGATCGGTCG ACAAATTCAA AGCTGCCAAG CGTTCGGAG                      39

(2) INFORMATION FOR SEQ ID NO: 17:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GCGGCCGCAA GCTTTGGCTC GAGCAATGGG GCCAGGCA                       38

(2) INFORMATION FOR SEQ ID NO: 18:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

GCGGCCGCAA GCTTAAGATG CTTGGAACCG CACCTGCCG                      39

(2) INFORMATION FOR SEQ ID NO: 19:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

CGATCGGTCG ACCAGATGAG CACATCATAG CGCTGATGA                      39

(2) INFORMATION FOR SEQ ID NO: 20:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

GCGGCCGCAA GCTTTGGCTC GAGCAATGGG GCCAGGCA                       38

(2) INFORMATION FOR SEQ ID NO: 21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear
```

-continued

```
   (ii) MOLECULE TYPE: DNA (genomic)

(xi) SEQUENCE DESCRIPTION: SEQ ID NO: 21:

GCGGCCGCAA GCTTAAGATG CTTGGAACCG CACCTGCCG                    39

(2) INFORMATION FOR SEQ ID NO: 22:

(i) SEQUENCE CHARACTERISTICS:
       (A) LENGTH: 39 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 22:

CGATCGGTCG ACAAATTCAA AGCTGCCAAG CGTTCGGAG                    39

(2) INFORMATION FOR SEQ ID NO: 23:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 23:

Asp Tyr Lys Asp Asp Asp Asp Lys
       1               5
```

EFFECTOR PROTEINS OF RAPAMYCIN

RELATED APPLICATIONS

This is continuation of application Ser. No. 08/471,112, filed Jun. 6, 1995, now U.S. Pat. No. 6,313,264, which is a continuation-in-part of patent application Ser. No. 08/384,524, filed Feb. 13, 1995, now abandoned, which is a continuation-in-part of patent application Ser. No. 08/312,023, filed Sep. 26, 1994, now abandoned, which is a continuation-in-part of patent application Ser. No. 08/207,975, filed Mar. 8, 1994, now abandoned, all of which are incorporated herein by reference.

This invention concerns effector proteins of Rapamycin. More particularly, this invention concerns novel Rapamycin-FKBP12 binding proteins of mammalian origin for identification, design and synthesis of immunomodulatory, anti-restenosis or anti-tumor agents.

BACKGROUND OF THE INVENTION

Rapamycin is a macrolide antibiotic produced by *Streptomyces hygroscopicus* which was first characterized via its properties as an antifungal agent. It adversely affects the growth of fungi such as *Candida albicans* and *Microsporum gypseum*. Rapamycin, its preparation and its antibiotic activity were described in U.S. Pat. No. 3,929,992, issued Dec. 30, 1975 to Surendra Sehgal et al. In 1977 Martel, R. R. et al. reported on immunosuppressive properties of rapamycin against experimental allergic encephalitis and adjuvant arthritis in the Canadian Journal of Physiological Pharmacology, 55, 48–51 (1977). In 1989, Calne, R. Y. et al. in Lancet, 1989, no. 2, p. 227 and Morris, R. E. and Meiser, B. M. in Medicinal Science Research, 1989, No. 17, P. 609–10, separately reported on the effectiveness of rapamycin in inhibiting rejection in vivo in allograft transplantation. Numerous articles have followed describing the immunosuppressive and rejection inhibiting properties of rapamycin, and clinical investigation has begun for the use of rapamycin in inhibiting rejection in transplantation in man.

Rapamycin alone (U.S. Pat. No. 4,885,171) or in combination with picibanil (U.S. Pat. No. 4,401,653) has been shown to have antitumor activity. R. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions. U.S. Pat. No. 5,118,678 discloses carbamates of rapamycin that are useful as immunosuppressive, anti-inflammatory, antifungal, and antitumor agents. U.S. Pat. No. 5,100,883 discloses fluorinated esters of rapamycin. U.S. Pat. No. 5,118,677 discloses amide esters of rapamycin. U.S. Pat. No. 5,130,307 discloses aminoesters of rapamycin. U.S. Pat. No. 5,117,203 discloses sulfonates and sulfamates of rapamycin. U.S. Pat. No. 5,194,447 discloses sulfonylcarbamates of rapamycin.

U.S. Pat. No. 5,100,899 (Calne) discloses methods of inhibiting transplant rejection in mammals using rapamycin and derivatives and prodrugs thereof. Other chemotherapeutic agents listed for use with rapamycin are azathioprine, corticosteroids, cyclosporin (and cyclosporin A), and FK-506, or any combination thereof.

Rapamycin produces immunosuppressive effects by blocking intracellular signal transduction. Rapamycin appears to interfere with a calcium independent signalling cascade in T cells and mast cells [Schreiber et al. (1992) Tetrahedron 48:2545–2558]. Rapamycin has been shown to bind to certain immunophilins which are members of the FK-506 binding proteins (FKBP) family. In particular, Rapamycin has been shown to bind to the binding proteins, FKBP12, FKBP13, FKBP25 [Galat A. et al., (1992) Biochemistry 31(8);2427–2437 and Ferrera A, et al., (1992) Gene 113(1):125–127; Armistead and Harding, Ann. Reports in Med. Chem. 28:207–215, 1993], and FKBP52 [WO 93/07269]

Rapamycin is able to inhibit mitogen-induced T cell and B cell proliferation as well as proliferation induced by several cytokines, including IL-2, IL-3, IL-4 and IL-6 (reviewed by Sehgal et al., Med. Research Rev.14: 1–22, 1994). It can also inhibit antibody production. Rapamycin has been shown to block the cytokine-induced activation of $p70^{S6}$ kinase which appears to correlate with Rapamycin's ability to decrease protein synthesis accompanying cell cycle progression (Calvo et al., Proc. Natl. Acad. Sci. USA, 89:7571–7575, 1992; Chung et al., Cell 69:1227–1236, 1992; Kuo et al., Nature 358:70–73, 1992; Price et al., Science 257:973–977, 1992). It also inhibits the activation of cdk2/cyclin E complex (Flanagan et al., Ann. N.Y.Acad. Sci, 30;696:31–37, 1993 Flanagan et al., J.Cell Biochem. 17A:292, 1993). Rapamycin's effects are not mediated by direct binding to $p70^{s6}$ kinase and cdk2/cyclin E, but by action of the Rapamycin-FKBP complex on upstream component(s) which regulate the activation status of the kinases.

It is generally accepted that the action of immunosuppressive drugs, such as Rapamycin, cyclosporine and FK506, is dependent upon the formation of a complex with their respective intracellular receptor proteins called immunophilins. While the binding of these immunosuppressants with their respective immunophilins inhibits the cis-trans peptidyl prolyl isomerase (PPIase) activity of immunophilins, PPIase inhibition is not sufficient to mediate the immunosuppressive activity (reviewed in Armistead and Harding, Annual Reports in Med. Chem, 28:207–215:1993). Two rapamycin analogs which are Diels Alder adducts, one with 4-phenyl-1,2,4-triazoline-3,5-dione, and the second with 4-methyl-1,2,4-triazoline-3,5-dione, bind to FKBP, inhibited its PPIase activity, yet they did not exhibit any detectable immunosuppressive activity. The phenyltriazolinedione Diels Alder adduct at high molar excess has been shown to competitively inhibit rapamycin's effect on DNA synthesis in mitogen-stimulated stimulated murine thymocyte proliferation (Ocain et al., Biochem. Biophys. Res. Commun. 192:1340, 1993). Recent evidence suggests that the binary immunophilin-drug complex such as cyclophilin-cyclosporin A and FKBP-FK506 gains a new function that enables it to block signal transduction by acting on specific target proteins. The molecular target of both cyclophilin-cyclosporin A and FKBP-FK506 complexes such as has been identified as the $Ca^{+2}$/calmodulin dependent serine/threonine phosphatase calcineurin (J. Liu et al, Cell 66, 807, 1991; J. Liu et al, Biochemistry 31, 3896, 1992; W. M. Flanagan, et al., Nature 352, 803, 1992; McCaffrey et al., J. Biol. Chem. 268, 3747, 1993; McCaffrey et al., Science 262:750, 1993).

Rapamycin's antifungal and immunosuppressive activities are mediated via a complex consisting of Rapamycin, a member of the FK506 binding protein (FKBP) family and at least one additional third protein, called the target of Rapamycin (TOR). The family of FKBPs is reviewed by Armistead and Harding (Annual Reports in Med. Chem, 28:207–215:1993). The relevant FKBP molecule in Rapamycin's antifungal activity has been shown to be FKBP12 (Heitman et al., Science 253:905–909:1993). In mammalian cells, the relevant FKBPs are being investigated. Although two TOR proteins (TOR1 and TOR2) have been identified in yeast (Kunz et al., Cell 73:585–596:1993), the target of Rapamycin in human cells remains elusive. The carboxy terminus of yeast TOR2 has been shown to exhibit 20% identity with two proteins, the p110 subunit of phosphatidylinositol 3-kinase and VPS34, a yeast vacuolar sorting protein also shown to have PI 3K activity. However, J. Blenis et al. (Joint Meeting of the American Association of Immunologists and The Clinical Immunology Society, Denver, Colo., May, 1993) have reported that Rapamycin-FKBP12 complex does not directly mediate its effects on PDGF stimulated cells via the p110, p85 PI 3K complex.

DESCRIPTION OF THE INVENTION

This invention concerns isolated, cloned and expressed proteins which bind to a complex of GST-FKBP12-Rapamycin. These proteins are isolated from membrane preparations of Molt 4 T cell leukemia. The sizes of the four novel proteins are estimated by PAGE migration to be 125±12 kilodaltons (kDa), 148±14 kDa, 208±15 kDa and 210±20 kDa and will be referred to herein and in the claims that follow, as the 125 kDa, 148 kDa, 208 kDa, and 210 kDa, respectively. The four proteins may also be referred to herein as effector proteins.

The proteins of this invention can be used in screening assays, such as enzyme inhibitor assays and binding assays, to identify endogenous complexes and ligands and novel exogenous compounds (like Rapamycin) which modulate their functions. They can also be used in assays to identify compounds with therapeutic benefit for restenosis, immunomodulation and as antitumor agents. Cloning the proteins of this invention does not only allow the production of large quantities of the proteins, it also provides a basis for the development of related anti-sense therapeutics. The use of cDNA clones to generate anti-sense therapeutics with immunomodulatory activity (for use against transplantation rejection, graft versus host disease, autoimmune diseases such as lupus, myasthenia gravis, multiple sclerosis, rheumatoid arthritis, type I diabetes, and diseases of inflammation such as psoriasis, dermitis, eczema, seborrhea, inflammatory bowel disease, pulmonary inflammation, asthma, and eye uveitis), antirestenosis and anti-tumor activity is included within the scope of this invention.

The proteins of the present invention can be isolated from mammalian cells, such as cells of the T cell leukemia cell line, Molt 4 (ATCC 1582, American Type Cell Culture, 12301 Parklawn Drive, Rockville, Md., USA, 20852), the B cell lymphoma, BJAB, or normal human T cells. These mammalian cells can be lysed in a buffer containing protease inhibitors and reducing agent (2-ME), such as hypotonic buffer A (100 mM HEPES, pH 7.5, 20 mM KCl, 1 mM EDTA, 0.4 mM PMSF and 2 mM beta mercaptoethanol (2-ME)). The cell nuclei and unbroken cells are cleared by centrifugation at a temperature which minimizes protein degradation. The membrane fraction of the cells can then be concentrated or pelleted by ultracentrifugation at 100,000 g. Detergent solubilization of the membrane pellet is carried out in a detergent containing buffer such as buffer B (50 mM Tris, pH 7.2, 100 mM NaCl, 20 mM KCl, 0.2 mM PMSF, 1 mM 2-ME, 2 mM $CaCl_2$, 2 mM $MgCl_2$, 5 µg/ml aprotinin, leupeptin, pepstatin A and antipain), containing CHAPSO (3-[(3-cholamido-propyl)dimethylammonio]-1-propane sulfonate; 12 mM) or Tritonx100 (polyethylene glycol 4-isooctylphenyl ether). The solubilized membrane proteins can then be separated from the debris by 1,000,000 g ultracentrifugation at a temperature which minimizes protein degradation. The supernatant containing solubilized membrane proteins is then preabsorbed with an affinity resin, such as glutathione resin, in the presence of protease inhibitors at a temperature which minimizes protein degradation. After centrifugation to remove the resin from the supernatant, the supernatant is then incubated with complexed Rapamycin or Rapamycin analog to FKBP, such as GST-FKBP12-Rapamycin at a temperature which minimizes protein degradation. The mixture of solubilized membrane proteins, incubated with complexed Rapamycin or Rapamycin analog to FKBP, such as GST-FKBP12-Rapamycin, can then be incubated with the affinity resin to bind the complexes of rapamycin or rapamycin analog, FKBP fusion protein and binding proteins at a temperature which minimizes protein degradation. After most non-specific proteins are rinsed away using a detergent containing buffer, such as Buffer C (50 mM Tris, pH 7.2, 100 mM NaCl, 20 mM KCl, 0.2 mM PMSF, 1 mM 2-ME or 10 mM dithiothreitol, 0–5 mM $CaCl_2$, 0–5 mM $MgCl_2$, 5 µg/ml aprotinin, leupeptin, pepstatin A and antipain and 0.1% Tritonx100) (Polyethylene glycol 4-isooctyl phenyl ether), the proteins are eluted from the resin under denaturing conditions, such as a buffer containing sufficient detergent to dissociate it from resin (e.g. Laemli buffer with or without glycerol or dye, as described by Laemli, Nature 227:680, 1970), or non-denaturing conditions such as a buffer containing an appropriate eluting compound for the affinity column, such as 5 mM glutathione. The proteins can then be separated by size using SDS polyacrylamide gel electrophoresis (SDS-PAGE).

The present invention also includes the genomic DNA sequences for the abovementioned proteins, as well as the cDNA and anti-sense RNA and DNA sequences which correspond to the genes for the abovementioned proteins. The present invention further includes the proteins of other mammalian species which are homologous or equivalent at least in function to the abovementioned proteins, as well as the DNA gene sequences for the homologous or equivalent proteins and the cDNA and anti-sense RNA and DNA sequences which correspond to the genes for the homologous or equivalent proteins.

For the purposes of this disclosure and the claims that follow, equivalents of the proteins of this invention are considered to be proteins, protein fragments and/or truncated forms with substantially similar, but not identical, amino acid sequences to the proteins mentioned above, the equivalents exhibiting rapamycin-FKBP complex binding characteristics and function similar to the proteins mentioned above. Therefore, in this specification and the claims below, references to the 125 kDa, 148 kDa, 208 kDa, and 210 kDa proteins of this invention are also to be understood to indicate and encompass homologous or equivalent proteins, as well as fragmented and/or truncated forms with substantially similar, but not identical, amino acid sequences of the 125 kDa, 148 kDa, 208 kDa, and 210 kDa proteins mentioned above.

These proteins or protein homologues or equivalents can be generated by similar isolation procedures from different cell types and/or by recombinant DNA methods and may be modified by techniques including site directed mutagenesis. For example, the genes of this invention can be engineered to express one or all of the proteins as a fusion protein with the fusion partner giving an advantage in isolation (e.g. HIS oligomer, immunoglobulin Fc, glutathione S-transferase, FLAG etc). Mutations or truncations which result in a soluble form can also be generated by site directed mutagenesis and would give advantages in isolation.

This invention further includes oligopeptide fragments, truncated forms and protein fragments that retain binding affinity yet have less than the active protein's amino acid sequences. This invention also includes monoclonal and polyclonal antibodies specific for the proteins and their uses. Such uses include methods for screening for novel agents for immunomodulation and/or anti-tumor activity and methods of measuring the parent compound and/or metabolites in biological samples obtained from individuals taking immunosuppressive drugs. The use of the cDNA clone to generate anti-sense therapeutics (Milligan et al, J. Med. Chem. 36:1923–1936, 1993) with immunomodulatory activity (transplantation rejection, graft versus host disease, autoimmune diseases such as lupus, myasthenia gravis, multiple sclerosis, rheumatoid arthritis, type I diabetes, and diseases of inflammmation such as psoriasis, dermitis, eczema, seborrhea, inflammatory bowel disease, pulmonary inflammation, asthma, and eye uveitis), and anti-tumor activity is also included in the present invention.

The proteins of this invention can also be made by recombinant DNA techniques familiar to those skilled in the art. That is, the gene of the protein in question can be cloned by obtaining a partial amino acid sequence by digestion of the protein with a protease, such as Lysine C, and isolating the resulting protein fragments by microbore HPLC, followed by fragment sequencing (Matsudaira in A Practical Guide to Protein and Peptide Purification for Microsequencing, Academic Press (San Diego, Calif., 1989)). The determined sequence can then be used to make oligonucleotide probes which can be used to screen a human cDNA library directly or generate probes by polymerase chain reaction. The library can be generated from human T cells or the cell lines, Molt 4, Jurkat, or other etc. to obtain clones. These clones can be used to identify additional clones containing additional sequences until the protein's full gene, i.e. complete open reading frame, is cloned.

It is known in the art that some proteins can be encoded by an open reading frame which is longer than initially predicted by the size of the protein. These proteins may represent cleavage products of the precursor protein translated from the complete open reading frame (eg. IL-1 beta) or proteins translated using a downstream start codon (eg. Hepaptitis B surface antigen). In view of this knowledge, it is understood that the term cDNA as used herein and in the claims below refers to cDNA for the gene's complete open reading frame or any portions thereof which may code for a protein of this invention or the protein's fragments, together or separate, or truncated forms, as previously discussed.

In a complementary strategy, the gene(s) for the proteins of this invention may be identified by interactive yeast cloning techniques using FKBP12:RAPA as a trap for cloning. These strategies can also be combined to quicken the identification of the clones.

The relevant cDNA clone encoding the gene for any of the four proteins can also be expressed in $E.\ coli$, yeast, or baculovirus infected cells or mammalian cells using state of the art expression vectors. Isolation can be performed as above or the cDNA can be made as a fusion protein with the fusion partner giving an advantage in isolation (e.g. HIS oligomer, immunoglobulin Fc, glutathione S-transferase, etc). Mutations which result in a soluble form can also be generated by site directed mutagenesis and would give advantages in isolation.

The uses of such cDNA clones include production of recombinant proteins. Further, such recombinant proteins, or the corresponding natural proteins isolated from mammalian cells, or fragments thereof (including peptide oligomers) are useful in generation of antibodies to these proteins. Briefly, monoclonal or polyclonal antibodies are induced by immunization with recombinant proteins, or the corresponding natural proteins isolated from mammalian cells, or fragments thereof (including peptide oligomers conjugated to a carrier protein (e.g. keyhole limpet hemocyanin or bovine serum albumin)) of animals using state of the art techniques. The antibodies can be used in the purification process of the natural proteins isolated from mammalian cells or recombinant proteins from $E.\ coli$, yeast, or baculovirus infected cells or mammalian cells, or cell products.

The uses of such cDNA clones include production of recombinant proteins. Further, such recombinant proteins, or the corresponding natural proteins isolated from mammalian cells, are useful in methods of screening for novel agents such as synthetic compounds, natural products, exogenous or endogenous substrates for immunomodulation and/or antitumor activity. The natural products which may be screened may include, but are not limited to, cell lysates, cell supernatants, plant extracts and the natural broths of fungi or bacteria. As an example of a competitive binding assay, one of these proteins attached to a matrix (either covalently or noncovalently) can be incubated with a buffer containing the compounds, natural products, cell lysates or cell supernatants and a labeled rapamycin:FKBP complex. The ability of the compound, natural products, exogenous or endogenous substrates to competitively inhibit the binding of the complex or specific antibody can be assessed. Examples of methods for labeling the complex include radiolabeling, fluorescent or chemiluminescent tags, fusion proteins with FKBP such as luciferase, and conjugation to enzymes such as horse radish peroxidase, alkaline phosphatase, acetylcholine esterase (ACHE), etc. As an example of an enzymatic assay, the proteins are incubated in the presence or absence of novel agents such as synthetic compounds, natural products, exogenous or endogenous substrates with substrate and the enzymatic activity of the protein can be assessed. Methods of measuring the parent compound and/ or metabolites in biological samples obtained from individuals taking immunosuppressive drugs can also be assessed using these proteins.

This invention includes a method for identifying substances which may be useful as immunomodulatory agents or anti-tumor agents, the method utilizing the following steps:

a) combining the substance to be tested with one of the four mammalian proteins (125 kDa, 148 kDa, 208 kDa or 210 kDa) of this invention, with the protein being bound to a solid support:

b) maintaining the substance to be tested and the protein bound to the solid support of step (a) under conditions appropriate for binding of the substance to be tested with the protein, and c) determining whether binding of the substance to be tested occurred in step (b).

This invention also includes a method for identifying substances which may be useful as immunomodulatory or anti-tumor agents which involves the following steps:

a) combining a substance to be tested with one of the mammalian proteins of this invention, the protein being bound to a solid support:

b) maintaining the substance to be tested and the protein bound to the solid support of step (a) under conditions appropriate for binding of the substance to be tested with the protein, and c) determining whether the presence of the substance to be tested modulated the activity of the mammalian protein.

This invention further includes a method for detecting, in a biological sample, rapamycin, rapamycin analogs or rapamycin metabolites which, when complexed with a FKBP, bind to one of the four listed proteins of this invention, the method comprising the steps of:

a) combining the biological sample with a FKBP to form a first mixture containing, if rapamycin, rapamycin analogs or rapamycin metabolites are present in the biological sample, a rapamycin:FKBP complexes, rapamycin analog:FKBP complexes, or rapamycin metabolite:FKBP complexes;

b) creating a second mixture by adding the first mixture to one of the proteins of this invention, the protein bound to a solid support;

c) maintaining the second mixture of step (b) under conditions appropriate for binding the rapamycin-:FKBP complexes, rapamycin analog:FKBP complexes, or rapamycin metabolite:FKBP complexes, if present, to the protein of this invention; and d) determining whether binding of the rapamycin:FKBP complexes, rapamycin analog:FKBP complexes, or rapamycin metabolite:FKBP complexes and the protein occurred in step (c).

Also included in this invention is the use of the cDNA clones to generate anti-sense therapeutics. This can be accomplished by using state of the art techniques, such as those described in Milligan et al, J. Med. Chem. 36:14:1924–1936, 1993. For the purposes of this disclosure and the claims that follow, antisense RNA and DNA are understood to include those RNA and DNA strands derived from a cDNA clone which encodes for one of the four proteins (125 kDa, 148 kDa, 208 kDa or 210 kDa) of the present invention which have a native backbone or those which utilize a modified backbone. Such modifications of the RNA and DNA backbones are described in Milligan et al, J. Med. Chem. 36:14:1924–1936, 1993. The antisense compounds created by the state of the art techniques recently described (Milligan et al, J. Med. Chem. 36:14:1924–1936, 1993) can be useful in modulating the immune response and thus useful in the treatment or inhibition of transplantation rejection such as kidney, heart, liver, lung, bone marrow, pancreas (islet cells), cornea, small bowel, and skin allografts, and heart valve xenografts; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis. The antisense molecules of this invention can have antitumor, antifungal activities, and antiproliferative activities. The compounds of this invention therefore can be also useful in treating solid tumors, adult T-cell leukemia/lymphoma, fungal infections, and hyperproliferative vascular diseases such as restenosis and atherosclerosis. Thus, the present invention also comprises methods for treating the abovementioned maladies and conditions in mammals, preferably in humans. The method comprises administering to a mammal in need thereof an effective amount of the relevant antisense therapeutic agent of this invention.

When administered for the treatment or inhibition of the above disease states, the antisense molecules of this invention can be administered to a mammal orally, parenterally, intranasally, intrabronchially, transdermally, topically, intravaginally, or rectally.

It is contemplated that when the antisense molecules of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the complexes of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

Treatment with these antisense compounds will generally be initiated with small dosages less than the optimum dose of the compound. Thereafter the dosage is increased until the optimum effect under the circumstances is reached. Precise dosages will be determined by the administering physician based on experience with the individual subject treated. In general, the antisense compounds of this invention are most desirably administered at a concentration that will afford effective results without causing any harmful or deleterious side effects.

In light of the therapeutic value of the abovementioned antisense compounds, this invention also includes pharmaceutical compositions containing the antisense RNA and antisense DNA compounds derived from cDNA clones which encode for the 125 kDa, 148 kDa, 208 kDa and 210 kDa proteins of this invention.

This invention also comprises the following process for isolating the proteins of this invention, as well as the proteins isolated therefrom:

A process for isolating proteins from mammalian cells, the process comprising the steps of:

1. The mammalian cells of interest are grown and harvested. As mentioned previously, the cells may be of T cell origin (e.g. T cell lymphomas, leukemias, normal human T cells), B cell origin (e.g. EBV transformed B cells, normal human B cells), mast cells, or other cell sources sensitive to rapamycin. The cells may be processed shortly after harvesting or may be stored frozen, such as in pellets, prior to processing. The cells which are kept frozen may be stored in a dry ice and ethanol bath, stored frozen at −70–80° C. until use. This step of growing and harvesting the cells of interest may be seen as the first step of this process or as merely preparatory for the present process.

2. Cells are lysed in a buffer containing a buffering agent (e.g.HEPES, Tris, pH 7.5), low salt (e.g.10–50 mM NaCl or KCl), chelating agent (e.g. 1–2 mM EDTA), protease inhibitors (e.g.0.4 mM PMSF) and a reducing agent (e.g. 2 mM 2-ME or 1–20 mM Dithiothreitol) at a temperature which minimizes protein degradation (e.g. 4° C.). It should be understood that the mammalian cells may be treated in any manner capable of producing cell lysis, including sonic lysis and douncing.

3. Unbroken cells and cell nuclei are precleared from lysates by centrifugation at a temperature which minimizes protein degradation (e.g. 4° C.). Centrifugation at, for example, 1600 g for 10 minutes has been found sufficient to preclear the unbroken cells and cell nuclei from the lysates. This step, while not mandatory, provides a clearer preparation for the steps that follow.

4. The membrane fraction in the precleared lysate is then concentrated, such as by ultracentrifugation. An example of this concentration would be ultracentrifugation at 100,000 g for 1–1.5 hours.

5. The membrane proteins (e.g. transmembrane, integral and membrane associated proteins) are then solubilized. This may be accomplished by incubating the pellet of Step 4 in a buffer containing a detergent which solubilizes the proteins without detrimentally denaturing them, a buffering agent (e.g. 20–50 mM Tris or HEPES, pH 7.2), salt (e.g. 100–200 mM NaCl+20 mM KCl), reducing agent (e.g. 1–2 mM 2-ME or 1–20 mM dithiothreitol), protease inhibitors (e.g. 0.2 mM PMSF, 5 μg/ml aprotinin, leupeptin, pepstatin A and antipain), divalent cations (e.g. 0–5 mM $CaCl_2$, 0–5 mM $MgCl_2$) at a temperature which minimizes protein degradation (e.g. 4° C.). Examples of detergents useful in this step are CHAPSO (3-[(3-cholamidopropyl)dimethylammonio]-1-propane sulfonate) or Triton×100 (polyethylene glycol 4-isooctylphenyl ether). After this step, the mixture contains solubilized membrane proteins and non-solubilized cellular debris.

6. The solubilized membrane proteins are separated from the non-solubilized cellular debris, such as by ultracentrifugation (eg 100,000 for 1–1.5 hours) at a temperature which minimizes protein degradation (e.g. 4° C.).

7. The supernatant containing solubilized membrane proteins is incubated with an affinity resin in a buffer containing a buffering agent (e.g.20–50 mM Tris or HEPES, pH 7.2), salt (e.g. 100–200 mM NaCl+20 mM KCl), reducing agent (e.g. 1–2 mM 2-ME or 10–20 mM dithiothreitol), protease inhibitors (e.g. 0.2 mM PMSF, 5 μg/ml aprotinin, leupeptin, pepstatin A and antipain), divalent cations (e.g. 0–5 mM $CaCl_2$, 0–5 mM $MgCl_2$) at a temperature and time which allows the absorption of the proteins which bind to affinity resin directly, and minimizes protein degradation (e.g. 4° C.).

8. The resin is then removed from the supernatant by centrifugation at a temperature which minimizes protein degradation (e.g. 4° C.).

9. The supernatant is then incubated with Rapamycin or Rapamycin analog (IC50 in LAF<500 nM) complexed to fusion protein of FKBP12+protein which enhances the isolation of the desired effector protein and through which the fusion protein binds to an affinity resin or affinity column, such as GST-FKBP12, Histidine oligomer-FKBP12, biotin-FKBP12, etc., in a buffer containing a buffering agent (e.g. 20–50 mM Tris or HEPES, pH 7.2), salt (e.g. 100–200 mM NaCl+20 mM KCl), reducing agent (e.g. 1–2 mM 2-ME or 1–20 mM dithiothreitol), protease inhibitors (e.g. 0.2 mM PMSF, 5 μg/ml aprotinin, leupeptin, pepstatin A and antipain), divalent cations (e.g. 0–5 mM $CaCl_2$, 0–5 mM $MgCl_2$) at a temperature and for a time which allows binding of the effector proteins to the fusion FKBP protein:Rapamycin or analog complexes and minimizes protein degradation (e.g. 4° C. and 1–2 hours).

10. The mixture of Step 9 containing the effector proteins and fusion FKBP protein:Rapamycin complexes is incubated with an affinity resin at a temperature and for a time which allows binding of the complexes of the effector proteins and fusion FKBP protein:Rapamycin or analog to the affinity resin and minimizes protein degradation (e.g. 4° C. and 0.5–2 hours).

11. Most non-specific proteins are rinsed away from the resin using a buffer which dissociates binding of non-specific proteins but not the complex between the desired proteins and RAPA-FKBP, such as a buffer containing a buffering agent (e.g.20–50 mM Tris or HEPES, pH 7.2), salts (e.g. 100–1000 mM NaCl, KCl), reducing agent (e.g. 1–2 mM 2-ME or 10–20 mM dithiothreitol), protease inhibitors (e.g. 0.2 mM PMSF, 5μg/ml aprotinin, leupeptin, pepstatin A and antipain), divalent cations (e.g. 0–5 mM $CaCl_2$, 0–5 mM $MgCl_2$) and detergent which dissociates binding of non-specific proteins but not the complex between the four proteins and RAPA-fusion FKBP protein such as Triton×100 (Polyethylene glycol 4-isooctyl phenyl ether).

12. The effector proteins and the fusion FKBP protein:Rapamycin complexes are eluted from the resin using an appropriate buffer, such as a buffer containing sufficient detergent to dissociate it from resin (e.g. Laemli buffer with or without glycerol or dye, Laemli, Nature 227:680, 1970), or an appropriate eluting compound for the affinity column, such as glutathione, histidine.

13. The effector proteins can then be separated by size. This may be accomplished in any manner which separates the proteins by size, including, but not limited to, polyacrylamide gel electrophoresis and size exclusion column chromatography.

It might also be useful to compare the proteins isolated by a control procedure, that is a procedure which substitutes buffer for the rapamycin or rapamycin analog with an $IC_{50}$ in LAF<500 nM in step 8, can be used to more easily distinguish proteins which bind to the rapamycin:FKBP complex.

The proteins of this invention can also be made by recombinant DNA techniques familiar to those skilled in the art. That is, the gene of the protein in question can be cloned by obtaining a partial amino acid sequence by digestion of the protein with an appropriate endopeptidase, such as Lysine C, and isolating the resulting protein fragments by microbore HPLC, followed by fragment sequencing (Matsudaira in A Practical Guide to Protein and Peptide Purification for Microsequencing, Academic Press, San Diego, Calif. 1989). The determined sequence can then be used to make oligonucleotide probes which can be used to screen a human cDNA library, such as those for human T cells, Molt 4, Jurkat, etc, to obtain clones. (Sambrook, Fritsch, and Maniatas, Molecular Cloning, A Laboratory Manual, Cold Spring Harbor Press, 1989) These clones can be used to identify additional clones containing additional sequences until the protein's full gene is cloned (Sambrook, Fritsch, and Maniatas, Molecular Cloning, A Laboratory Manual, Cold Spring Harbor Press, 1989). In a complementary strategy, the gene(s) may be identified by interactive yeast cloning techniques using FKBP12:RAPA as a trap for cloning (Chien et al., Proc. Natl. Acad. Sci. 88: 9578–9582, 1991). These strategies can also be combined to quicken the identification of the clones.

The relevant cDNA clone can also be expressed in E. coli, yeast, or baculovirus infected cells or mammalian cells using state of the art expression vectors. Isolation can be performed as above or the cDNA can be made as a fusion protein with the fusion partner giving an advantage in isolation (e.g. HIS oligomer, immunoglobulin Fc, glutathione S-transferase, etc). Mutations which result in a soluble form can also be generated by site directed mutagenesis and would give advantages in isolation.

Homologs in the mouse, rat, monkey, dog and other mammalian species can be obtained using similar procedures. In addition, upon isolation of the human clone of the proteins, the clone can be used to screen for homologs in other mammalian species. These homologs can also be used to develop binding assays and to set up high through put screening assays for compounds, endogenous ligands, exogenous ligands with immunomodulatory activity.

Compounds, endogenous ligands and exogenous ligands having such immunomodulatory activity would can be useful in modulating the immune response and thus useful in the treatment or inhibition of transplantation rejection such as kidney, heart, liver, lung, bone marrow, pancreas (islet cells), cornea, small bowel, and skin allografts, and heart valve xenografts; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis.

The compounds, endogenous ligands and exogenous ligands mentioned above can also have antitumor, antifungal activities, and antiproliferative activities. The compounds of this invention therefore can be also useful in treating solid tumors, adult T-cell leukemia/lymphoma, fungal infections, and hyperproliferative vascular diseases such as restenosis and atherosclerosis.

EXAMPLE 1

The proteins of the present invention were isolated utilizing a fusion protein of glutathione S-transferase-FK506 binding protein2 (GST-FKBP). GST-FKBP is produced by a recombinant E. coli containing the plasmid, pGEX-FKBP. The cells were grown, induced with IPTG and the fusion protein was isolated using standard technology described in D. B. Smith and K. S. Johnson, Gene 67, 31, 1988 and K. L. Guan and J. E. Dixon, Anal. Biochem. 192, 262, 1991. The solution containing glutathione and GST-FKBP12 was exchanged 5× using a Centricon 10 filtration unit (Amicon) to remove the glutathione and exchange the buffer.

Molt 4 cells ($1 \times 10^9$) were grown in standard media (RPMI 1640 containing 100 U/ml pennicillin, 100 ug/ml L-glutamine, 10% FCS). The cells were harvested and rinsed 3× with PBS (50 mM phosphate buffer, pH 7.0, 150 mM NaCl), flash frozen in dry-ice ethanol bath and stored at −80° C. On ice, the cells were thawed and lysed using a dounce homogenizer with B pestle in 5 ml of buffer A (10 mM Hepes, pH 7.5, 20 mM KCl, 1 mM EDTA, 0.4 mM PMSF and 2 mM 2-ME). After the debris was cleared by centrifugation at 1600 g for 10 min. and the membrane fraction was concentrated by 100,000 g centrifugation (1 hour), the 100,000 g pellet was incubated in 3 ml buffer B (50 mM Tris, pH 7.2, 100 mM NaCl, 20 mM KCl, 0.2 mM PMSF, 1 mM 2-ME, 2 mM $CaCl_2$, 2 mM $MgCl_2$, 5 μg/ml aprotinin, leupeptin, pepstatin A and antipain), containing 12 mM CHAPSO for two hours at 4° C. The solubilized membrane proteins were separated from the debris by a 100,000 g centrifugation. After preabsorption of the supernatant for 3–18 hours with 0.4 ml glutathione sepharose resin swollen in buffer B, the supernatant was incubated with complexed Rapamycin-GST-FKBP12 (preformed by incubation of 660 ug GST-FKBP+60 ug RAPA in buffer B for 1–2 hours, 4° C.) for two hours at 4° C. The supernatant was then incubated for 2 hours at 4° C. with 100 ul glutathione resin (1:1 Buffer B). Nonspecific proteins were rinsed 5× with buffer C (buffer B+0.1% Triton×100) and the proteins eluted from the resin in Laemli buffer by incubation at 95° C. for 3 minutes and microcentrifugation. The proteins were separated by size using a 7% SDS-PAGE followed by silver stain. Four bands corresponding to proteins of molecular weights of 210 kDa, 208 kDa, 148 kDa, and 125 kDa were present in higher concentrations in the sample containing RAPA+GST-FKBP12 vs GST-FKBP alone.

The mitogen-stimulated thymocyte proliferation assay called the LAF, can be inhibited by rapamycin or analogs such as demethoxyrapamycin and indicates relative activity of rapamycin analogs in immunosuppression. The same proteins were isolated using GST-FKBP complexed with the immunosuppressive analog, demethoxyrapamycin (Table1). The Diels Alder adducts bound to FKBP12 and inhibited PPIase activity of FKBP12 but did not exhibit detectable immunosuppressive activity and thus do not bind to the target of rapamycin. The use of these two compounds complexed with GST-FKBP12 in the analogous isolation procedure (ie. replacing rapamycin:GST-FKBP12) yielded background levels of the 210 kDa proteins (no rapamycin) (Table 1). FK506, is an immunosuppressive compound which binds to FKBP and and mediates at least some of its effects through the binding of the FK506-FKBP complex with calcineurin. FK506 when complexed with GST-FKBP in an analogous procedure yielded only background levels of the 210 kDa protein (Table 1).

TABLE 1

Comparison of Binding of Rapamycin Analog--FKBP12 complexes to 210 kDa Protein

| Compound | 210 kDa | LAF | PPIase(Ki) |
| --- | --- | --- | --- |
| RAPA | +++ | 6 nM | 0.12 nM |
| demethoxyrapamycin | +++ | 58 nM | 4.4 nM |
| Diels Alder adduct (phenyl) | ± | >1000 nM | 12 nM |
| Diels Alder adduct (methyl) | ± | >1000 nM | 12 nM |
| FK506 | ± | 3 nM* | 0.4 nM |
| none (FKBP) | ± | | |

(*mechanism of action is different)

It is known that rapamycin must bind to a member of the FKBP family in order to mediate its effects. To verify that the proteins of this invention bind to the complex RAPA-GST-FKBP and not individually to rapamycin or FKBP12, a modified isolation procedure was employed. The modification consists of using (1) a rapamycin-42-biotin glycinate ester in place of rapamycin (both exhibit equivalent immunosuppressive activity in the LAF assay), (2) no exogenous FKBP and (3) a strepatavidin-conjugated resin in place of glutathione-resin. Only background levels of the 210 kDa protein was isolated using this modified isolation procedure.

The 210 kDa protein was isolated using the GST-FKBP12-rapamycin complex from BJAB cells (B cell lymphoma) and normal human T lymphocytes purified by Ficoll-Hypaque and T cell columns.

The results of the partial amino acid composition analysis are set forth in Table 2, below. It should be noted that the percentage of the basic amino acids was not determined.

TABLE 2

| Peak Number | Component Name | Retention Time | Peak Area | Response Factor | Peak Height | Concentration No./50 µl |
|---|---|---|---|---|---|---|
| | | 9.38 | | | | |
| | | 11.09 | | | | |
| 1 | Asp/Asn | 12.06 | 12.47076 | 0.02344 | 0.05142 | 0.30 |
| 2 | Thr | 13.05 | 2.92898 | 0.00000 | 0.00985 | 0.068 |
| 3 | Ser | 13.78 | 6.43968 | 0.00000 | 0.01995 | 0.15 |
| | | 15.68 | | | | |
| 4 | Glu/Gln | 16.87 | 25.47273 | 0.00000 | 0.05285 | 0.59 |
| | Prp | 18.24 | | | | 0.14 |
| 5 | Gly | 22.35 | 21.50384 | 0.00000 | 0.04645 | 0.44 |
| | | 22.90 | | | | |
| 6 | Ala | 23.73 | 16.69160 | 0.00000 | 0.03113 | 0.36 |
| | | 26.06 | | | | |
| | | 28.81 | | | | |
| 7 | Val | 29.39 | 4.83196 | 0.00000 | 0.00605 | 0.11 |
| | Met | 32.28 | | | | |
| 8 | Ile | 34.10 | 3.00560 | 0.2326 | 0.00782 | 0.0699 |
| 9 | Leu | 35.09 | 5.73202 | 0.02331 | 0.01372 | 0.1383 |
| 10 | nLeu | 36.27 | 20.48232 | 0.02174 | 0.04286 | 0.4453 |
| 11 | Tyr | 38.33 | 1.44792 | 0.02618 | 0.00226 | 0.0379 |
| 12 | Phe | 40.05 | 1.25017 | 0.02703 | 0.00187 | 0.0338 |
| 13 | His | 47.79 | 1.50905 | 0.02553 | 0.00580 | 0.0385 |
| 14 | | 51.80 | 12.66136 | 0.00000 | 0.01960 | 0.0000 |
| 15 | Lys | 53.34 | 9.90767 | 0.02283 | 0.02274 | 0.2262 |
| Totals | | | 146.53645 | | 0.33436 | |
| Not Determined | | | 144.29 | | | |

EXAMPLE 2

The 210 kDa (210±20 kDa) protein of this invention was isolated from $4 \times 10^{11}$ Molt 4 cells using the affinity matrix protocol as described previously. Bound proteins were eluted from the affinity matrix with 1× Laemli buffer without glycerol and dye (0.0625 M Tris-HCl, ph6.8, 2% SDS, 0.37 M b-mercaptoethanol) and were concentrated 3 consecutive times by centrifugation using centricon 100 (Amicon, Beverly, Mass.) at 4° C. the first two times and at 18° C. the third time. The concentrated sample was eluted from the centricon 100 filter by incubating 2 hours at room temperature with an equal volume of 2× laemli buffer without glycerol and dye the first 2× and 2× laemli buffer the third time. The proteins in the sample were separated by PAGE on a 1.5 mm thick 7% polyacrylamide gel (38:1). The proteins were transferred to polyvinylidine difluoride, PVDF, (Biorad, Hercules, Calif.) in 10× Tris/glycine buffer (Biorad) containing 0.037% SDS at 50 mAmps at 4° C. overnight. The proteins on the PVDF were stained with amido black (Biorad) in 10% ethanol, 2% acetic acid and the appropriate band was excised, rinsed with PBS and water and stored frozen.

Sequencing

The protein (approx. 3 ug) on the PVDF membrane was digested in situ with typsin using a modification described by J. Fernandez et al, (Anal.Biochem. 201: 255-64, 1992). Briefly, the PVDF was cut into 1 mm² pieces, prewet, and the protein digested in a 100 mM Tris-HCl, pH buffer containing 10% acetonitrile, and 1% reduced triton (CalBiochem) with 0.2 ug trypsin at 37° C. for 6 hours followed by addition of 0.2 ug trypsin and incubation overnight. The fragments were eluted from the membrane by sonication and the buffer containing the fragments were separated by microfuge centifugation. The membranes were backextracted 2× (i.e., 50 ul buffer was added to membranes, sonicated, and centrifuged in a microfuge and solution pooled with the original buffer containing the eluted fragments.) The sample (140–145 ul) was separated by narrow bore high performance liquid chromatography using a Vydac C18 2.1 mm×150 mm reverse phase column on a Hewlett Packard HPLC 1090 with a 40 diode array detector as described previously by W.Lane et al, (J.Protein Chem., 10(2): 151–60, 1991). Multiple fractions were collected and measured for absorption at multiple wavelengths (210, 277 and 292 nm). Optimal fractions were chosen for sequencing based on resolution, symmetry, and ultraviolet absorption and spectra (210 nm, 277 nm and 292 nm). An aliquot (5%) of the optimal fractions was analyzed for homogeneity and length of fragment by matrix assisted laser desorption time of flight mass spectrometry, MALDE-TOF-MS, on a Finnigan lasermat. Selected optimal fractions were sequenced by automated Edman degradation on an Applied Biosystems 477A protein sequencer using microcartridge and manufacturer's recommended chemistry cycle.

Sequence Comparison

Comparison was performed using the Intelligenetics suite (Intelligenetics, Calif.)

Sequences

Utilizing the methods mentioned above, it was determined that the 210 kDa (210±20 kDa) protein of this invention contains peptide fragments, four of which have amino acid sequences as shown below:

a) ILLNIEHR SEQ ID NO:5;
B) LIRPYMEPILK SEQ ID NO:6;
c) DXMEAQE SEQ ID NO:7; and
d) QLDHPLPTVTHPQVTYAYM(K) SEQ ID NO:8.

Those skilled in the art will recognize the one-letter symbols for the amino acids in question (the definitions for which can also be seen at page 21 of the text *Biochemistry*, Third Edition, W.H. Freeman and Company,© 1988 by Lubert Stryer). Those so skilled will also understand that the X in sequence c) indicates an as yet unidentified amino acid and the parentheses in sequence d) indicates that the amino acid in the position in question is possibly lysine.

As mentioned previously, the present invention includes fragmented or truncated forms of the proteins mentioned herein. This includes proteins which have as part or all of their amino acid sequence one or more of the four sequences listed as a)-d), above. For the purposes of the claims, below, the proteins referred to as including one or more of the "internal amino acid sequences" are understood to be any protein which contains one of the sequences listed above, whether the protein is comprised wholly of one or more of the sequences a)-d) or whether one or more of the sequences mentioned above form any portion of the protein. This is understood to include all locations on the protein's amino acid sequence including, but not limited to, those sections of the protein which initiate and terminate the protein's amino acid chain.

These partial amino acid sequences were compared with sequences in the Genbank database. There was identity with the sequence, accession number L34075 (Brown et al., Nature 369, 756–758 (1994)). The cDNA of the SEP gene was cloned as follows: Two micrograms of Molt 4 cDNA (Clontech, Palo Alto, Calif.) in 1×PCR buffer (10 mM Tris-HCl, pH 8.3, 50 mM KCl, 1 mM MgCl, 200 μM dDATP, 200 μM dTTP, 200 μM dCTP, 200 μM dGTP; Perkin Elmer,) with 1 unit Taq polymerase (Perlin Elmer), was amplified by Polymerase chain reaction (PCR) at 94 C for 30 sec., 66 C for 4 mm for 30 cycles, 72 C for 10 mm by three separate reactions containing one of the following pairs of oligomers:

```
                                           SEQ ID NO:9
CGATCGGTCGACTGCAGCACTTTGGGGATTGTGCTCTC and SEQ ID NO:10
GCGGCCGCAGCTTTCTTCATGCATGACAACAGCCCAGGC; or SEQ ID NO:11
GCGGCCGCAAGCTTCAAGTATGCAAGCCTGTGCGGCAAGA and SEQ ID NO:12
CGATCGGTCGACACCTTCTGCATCAGAGTCAAGTGGTCA; or SEQ ID NO:13
GCGGCCGCAAGCTTCCTCAGCTCACATCCTTAGAGCTGCA and

SEQ ID NO:14
CGATCGGTCGACTTATTACCAGAAAGGGCACCAGCCAATATA.
```

The oligonucleotides were synthesized and isolated by methods previously described and known in the art (Chemical and Enzymatic Synthesis of Gene Fragments, ed. by H. G. Gassin and Anne Lang, Verlag Chemie, Fla., 1982). The resulting PCR products named SEP3, SEP4, and SEP5, respectively, were incubated at 15 C overnight in buffer containing T4 DNA ligase (1 unit) and 50 ng pcII which was modified to efficiently ligate PCR products (TA cloning kit, Invitrogen, San Diego, Calif.) to yield PCR-pcII ligated products. The PCR-pcII products were transformed into competent E. coil INValphaF cells obtained commercially from Invitrogen. Miniprep DNA was prepared using the Quiagen miniprep kits (Quiagen, Chatsworth, Calif.) and the clones containing the appropriate sized POR product were identified by restriction enzyme digestion with commercially available HindIII or Sal I, electrophoresis, and comparison to standards. Sep2 and Sep1 cDNA was made using the TimeSaver cDNA synthesis Kit (Pharmacia, Piscataway, N.J.) with the first strand synthesis reaction containing oligodT (0.13 μg) and 250 pmoles of

```
                                           SEQ ID NO:15
CGATCGGTCGACCAGATGAGCACATCATAGCGCTGATGA or

SEQ ID NO:16
CGATCGGTCGACAAATTCAAAGCTGCCAAGCGTTCGGAG,
``` respectively. Sep2 and Sep1 second strand synthesis was performed using the TimeSaver cDNA synthesis kit with the addition of 250 pmoles of

```
                                           SEQ ID NO:17
GCGGCCGCAAGCTTTGGCTCGAGCAATGGGGCCAGGCA or

SEQ ID NO:18
GCGGCCGCAAGCTTAAGATGCTTGGAACCGCACCTGCCG,
``` respectively. The Sep2 and Sep1 cDNA was then amplified by PCR using

```
                                           SEQ ID NO:19
CGATCGGTCGACCAGATGAGCACATCATAGCGCTGATGA and SEQ ID NO:20
GCGGCCGCAAGCTTTGGCTCGAGCAATGGGGCCAGGCA or SEQ ID NO:21
GCGGCCGCAAGCTTAAGATGCTTGGAACCGCACCTGCCG and

SEQ ID NO:22
CGATCGGTCGACAAATTCAAAGCTGCCAAGCGTTCGGAG,
``` respectively as described above. The Sep2 PCR products were cloned into pcII using the TA cloning kit (Invitrogen). The Sep 1 PCR products were digested with Hind III and Sal I, separated from the pcII vector by agarose electrophoresis. The Sep1 (HindIII-SalI) fragment was isolated using the Sephaglas bandprep kit from Pharmacia and cloned into the HindIII and Sal I sites of pUC19 as described (Sambrook et al., Molecular Cloning Cold Spring Harbor, 1989). Ligation of the isolated Sep2(HindIII, AspI) and Sep3(AspI, SalI) fragments or Sep4(HindIII, AccIII/MroI) and Sep5(AccIII/MroI, Sal I) fragments into pUC18(HindIII, SalI) vector and transformation of competent E. coli INValphaF cells (Invitrogen) was performed by techniques known to those skilled in the art (Sambrook et al., Molecular Cloning Cold Spring Harbor, 1989) to obtain pUC18-Sep 23 and pUC18-Sep45 which contain nucleotides 1468–5326 and 4964–7653, respectively, of the full length clone shown in the attached Sequence No. 1. Ligation of the pUC19-Sep1 (EcoRV, SalI), Sep2345 (EcoRV, SalI) fragments and transformation of competent E. coli INValphaF cells (Invitrogen) were performed by techniques known to those skilled in the art (as described by Sambrook et al., Molecular Cloning Cold Spring Harbor, 1989) to obtain the full length clone. The nucleic acid sequence coding for this protein and its amino acid sequence are shown in Sequence No. 1.

A fusion protein, called glutathione S transferase-sirolimus effector protein, GST-SEP, was engineered by subcloning the Sep4 and Sep5 fragments into the plasmid, pGEX-KG (Guan, K. and Dixon, J. E. (1991) Anal. Biochem. 192, 262–267) as follows. Briefly, Sep4 was digested with commercially available HindIII restriction enzyme, the restriction site was filled in with the Klenow fragment of DNA polymerase (Gibco), and the DNA was extracted with phenol-chloroform and ethanol precipitated using techniques known by those skilled in the art (Sambrook et al., Molecular Cloning Cold Spring Harbor, 1989). The SEP4 (HindIII-Klenow) was further digested with MroI restriction enzyme, separated from the pcII vector by agarose electrophoresis and isolated as the fragment SEP4-HindIII-Klenow-MroI. Sep5 fragment was prepared by digestion with SalI and MroI, separated from the pcII vector by agarose electrophoresis and isolated as the fragment SEP5-SalI-MroI. pGEX-KG (Guan, K. and Dixon, J. E. (1991) Anal. Biochem. 192, 262–267) was digested with Nco I, filled in with the Klenow fragment of DNA polymerase and the DNA was extracted with phenol-chloroform and ethanol precipitated, using techniques of those skilled in the art (Sambrook et al., Molecular Cloning Cold Spring Harbor, 1989). pGEX-KG (NcoI, Klenow) was further digested with Sal I, separated from the undigested vector by agarose electrophoresis and isolated as the vector pGEX-KG-NcoI-Klenow-SalI, using techniques of those skilled in the art. Ligation of the vector, pGEX-KG-NcoI-Klenow-SalI and Sep 4 (HindIII, MroI) and Sep5 (MroI, SalI) fragments and transformation into E. coli strain INValphaF cells (Invitrogen) using techniques of those skilled in the art yielded the plasmid, pGEX-Sep45. Other *E. coli* hosts such as BL21 can also be used The DNA and protein sequence of this fusion protein is shown in Sequence No. 2.

Flag sequences and kinase recognition domain of heart muscle kinase can be added at the amino terminal end, by methods known in the art (see Chen et al., Gene 1994 Feb. 11; 139 (1): 73–75) within SEP or at the carboxy terminus of SEP, SEP4,5 or other fragments using an oligonucleotide which includes the coding sequence for Asp Tyr Lys Asp Asp Asp Asp Lys SEQ ID NO:23. The fusion protein can be isolated by affinity chromatography with anti-flag specific antibodies using the commercially available kits from IBI, New Haven, Conn.

Transformed host cells containing sequences of this invention have been deposited with the American Type Culture Collection (ATCC), 12301 Parklawn Drive, Rockville, Md. 20852, USA, and have been given the ATCC designations listed below:

|   | Sequence | ATCC Designation |
|---|---|---|
| a) | pUC19-Sep1 (nucleotides 1–1785 of Sequence No. 1) | ATCC 69756 |
| b) | pUC18-Sep23 (nucleotides 1468–5326 of Sequence No. 1) | ATCC 69753 |
| c) | pUC18-Sep45 (nucleotides 4964–7653 of Sequence No. 1) | ATCC 69754 |
| d) | pUC19-Sep1–5 (ATCC 69756 1–7653 of sequence 1) | ATCC 69829 |
| e) | pGEX-Sep45 plasmids (Sequence 2) | ATCC 69755. |

EXAMPLE 3

The 210 kDa protein of this invention was also isolated by the techniques described in Example 1 utilizing the following rapamycin analogs:

a) 42-Deoxy-42-[1-(1,1-dimethylethoxy)-2-oxoethoxy] rapamycin (which is described in U.S. Pat. No. 5,233,036);

b) 42-[O-[(1,1-Dimethylethyl)dimethylsilyl]] rapamycin (described in U.S. Pat. No. 5,120,842);

c) Rapamycin 42-ester with N-[1,1-dimethylethoxy) carbonyl]-N-methylglycine (described in U.S. Pat. No. 5,130,307);

d) Rapamycin 42-ester with 5-(1,1-dimethylethoxy)-2-[[(1,1-dimethylethoxy)carbonyl]amino]-5-oxopentanoic acid ethyl acetate solvate three quarter hydrate (see U.S. Pat. No. 5,130,307);

e) Rapamycin 42-ester with N-[(1,1-dimethylethoxy) carbonyl]glycylglycine hydrate (see U.S. Pat. No. 5,130,307); and f) Rapamycin 42-ester with N2, N6-bis[(1,1-dimethylethoxy)carbonyl]-L-lysine (see U.S. Pat. No. 5,130,307).

What is claimed is:

1. An isolated protein having a molecular weight of about 210 kDa as determined by SDS-PAGE or fragment thereof, the protein made by a process comprising the steps of:
   (a) providing a sample of human cellular material;
   (b) preparing an extract of the cellular material comprising cell membrane proteins;
   (c) contacting the extract with an affinity reagent comprising a complex of:
      (i) rapamycin and
      (ii) FKBP12 under conditions which permit materials capable of specifically binding to the affinity reagent to bind thereto;
   (d) separating materials which do not bind to the affinity reagent from the affinity reagent and the materials bound thereto;
   (e) dissociating the materials bound to the affinity reagent therefrom; and
   (f) separating the protein having a molecular weight of about 210 kDa or fragment thereof from the other materials dissociated from the affinity reagent, wherein the 210 KDa protein or fragment thereof specifically binds to the rapamycin-FKBP12 complex.

2. An isolated protein having a molecular weight of about 210 kDa, as determined by SDS-PAGE, or a fragment thereof, wherein said protein is a rapamycin effector protein which can be obtained from a human, and wherein said protein or fragment binds to a complex comprising:
   a) FKBP12 and
   b) rapamycin.

3. The isolated protein of claim 1 or claim 2, wherein the about 210 kDa protein comprises the amino acid sequence set out in SEQ ID NO:3.

* * * * *

UNITED STATES PATENT AND TRADEMARK OFFICE
CERTIFICATE OF CORRECTION

PATENT NO. : 6,713,607 B2
DATED : March 30, 2004
INVENTOR(S) : Caggiano et al.

It is certified that error appears in the above-identified patent and that said Letters Patent is hereby corrected as shown below:

Title page,
Item [73], Assignee, after "Wyeth, Madison, NJ (US)", insert -- The Trustees of Columbia University in the City of New York, New York, NY (US) --.

Signed and Sealed this

Thirtieth Day of November, 2004

JON W. DUDAS
*Director of the United States Patent and Trademark Office*